United States Patent [19]

Scribner

[11] 4,003,911
[45] Jan. 18, 1977

[54] SELECTED 3-PYRROLIDINONES AND 2,4-PYRROLIDINDIONES
[75] Inventor: Richard Merrill Scribner, Wilmington, Del.
[73] Assignee: E. I. Du Pont de Nemours and Company, Wilmington, Del.
[22] Filed: Sept. 26, 1975
[21] Appl. No.: 617,054
[52] U.S. Cl. .................. 260/326.2; 260/240 R; 424/274; 260/326.47; 260/326.45
[51] Int. Cl.$^2$ ................................ C07D 207/24
[58] Field of Search ....... 260/326.2, 326.47, 240 R, 260/326.44, 326.45

[56] References Cited
UNITED STATES PATENTS 3,873,566    3/1975    Scribner .................... 260/326.44

*Primary Examiner*—Lewis Gotts
*Assistant Examiner*—D. R. Phillips
*Attorney, Agent, or Firm*—Anthony P. Mentis

[57] ABSTRACT

Certain 1,5-disubstituted 3-pyrrolidinones and 2,4-pyrrolidindiones have biological properties which resemble those of the natural prostaglandins. Exemplary is 7[N(3-hydroxy-n-octyl)-2,4-dioxopyrrolidin-5-yl] heptanoic acid methyl ester of the formula

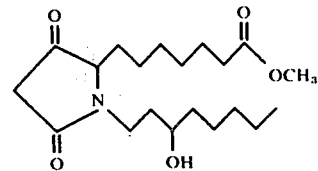

13 Claims, No Drawings

SELECTED 3-PYRROLIDINONES AND 2,4-PYRROLIDINDIONES

BACKGROUND OF THE INVENTION

1. Field of the Invention

This invention concerns substituted 3-pyrrolidinones and 2,4-pyrrolidindions whose biological properties resemble those of the natural prostaglandins. They may be considered as related to 12-azaprostaglandins.

2. Prior Art

Commonly assigned prior application Ser. No. 411,033 filed Oct. 30, 1973 and now U.S. Pat. No. 8,873,566 discloses 8,12-diazaprostaglandins and commonly assigned application Ser. No. 495,199 filed Aug. 6, 1974 discloses 8-azaprostaglandins. The compounds of this invention differ from those of these earlier applications in containing ketone carbonyl groups. The corresponding carbonyl groups in the earlier applications are amide carbonyl groups which impart different biological and chemical properties. Also the prepartory methods disclosed in the earlier applications do not produce the compounds of this invention.

STATEMENT OF THE INVENTION

There have now been discovered additional compounds, which resemble natural prostaglandins, of the general formula:

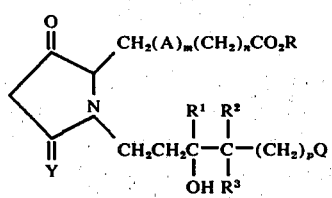

wherein
Y is O or $H_2$;
A is CH=CH, C≡C or phenylene;
$m$ is 0 or 1;
$n$ is 0–6;
R is H, alkali metal, amine salt, alkyl or cycloalkyl of up to 12 carbons;
$R^1$ is H, $CH_3$, $C_2H_5$, $CH=CH_2$ or C≡CH;
$R^2$ and $R^3$ individually are H, F, $CH_3$ or $C_2H_5$;
$p$ is 0–6; and
Q is $CH_3$, $CF_2CH_3$, $CF_3$, phenyl or phenyl substituted with up to two halogens or alkyls of 1–4 carbons; with the provisos that when $R^1$ is not H then $R^2$ and $R^3$ are each H; and that when Q is phenyl or substituted phenyl $p$ is 0–3.

The following are preferred because of their stability or relatively high biological activity, i.e. compounds where:

1. Y = $H_2$;
2. $m$ = 0 and $n$ = 5;
3. $m$ = 1 and $n$ = 2–4;
4. R is H, alkali metal, amine salt or alkyl or cycloalkyl of 1–4 carbons;
5. Q is $CH_3$ or $CF_3$ or $CF_3$ and $p$ = 3–5;
6. Q is $CF_2CH_3$ and $p$ = 2–4;
7. Q is phenyl or substituted phenyl and $p$ = 0–3.

In the structures above and in those that follow all the bonds to chiral carbon atoms which are respresented by solid lines (rather than by broken lines and wedges) indicate that each of the chiral carbon atoms of such compounds exists either (a) as mixtures of the two enantiomeric configurations or (b) exists in one absolute configuration, depending on whether optical resolutions have been carried out. Solid lines to chiral carbon atoms in themselves should be regarded as noncommittal with respect to configuration.

A. The 3-pyrrolidinones can be prepared by the following general synthetic sequence.

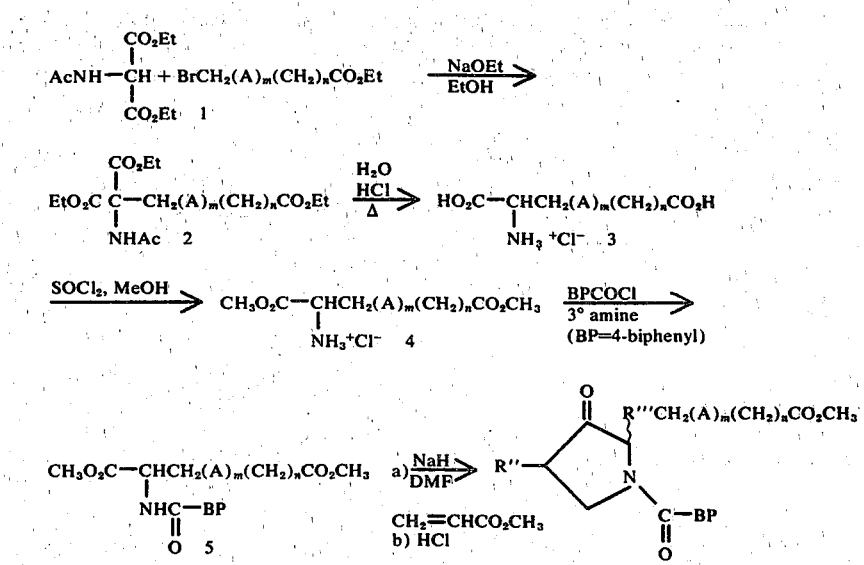

-continued
i R" = CO$_2$CH$_3$, R'" = H
ii R = H, R'" = CO$_2$CH$_3$
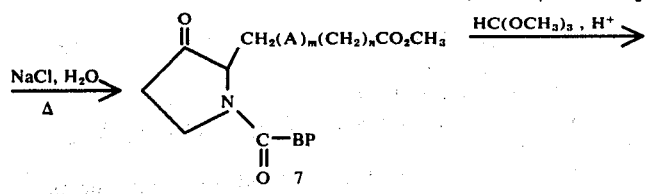
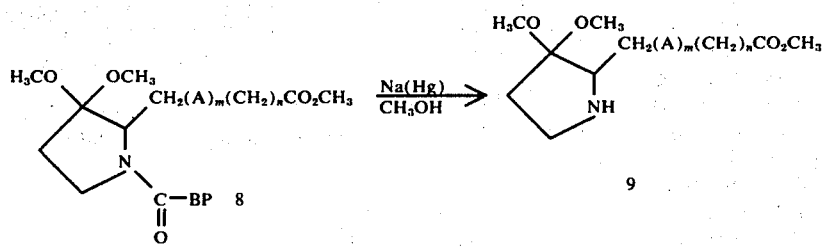
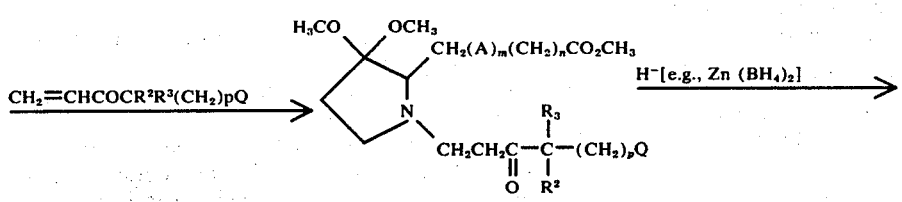
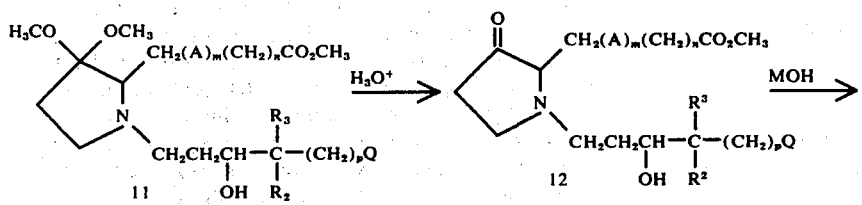
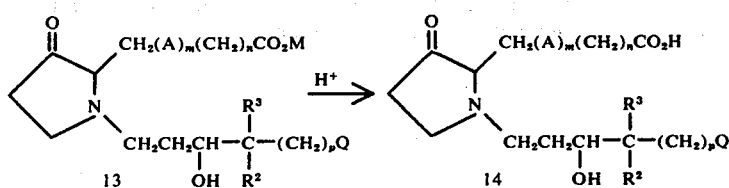
By conventional synthetic methods the intermediates indicated above can be converted to the other related compounds included in the general formula above. For example, for the higher esters corresponding to 12 the following method can be used:
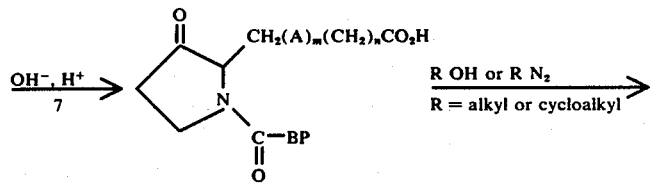
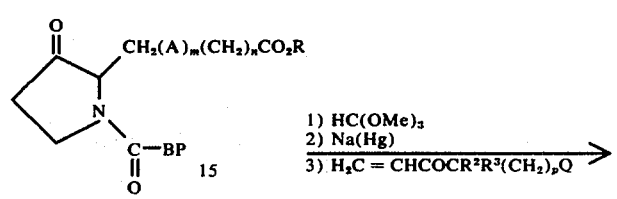

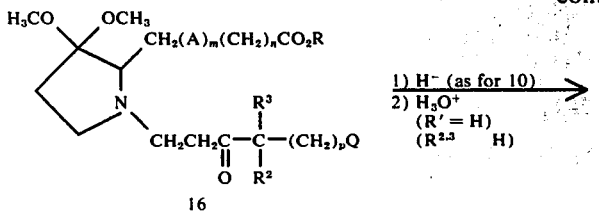

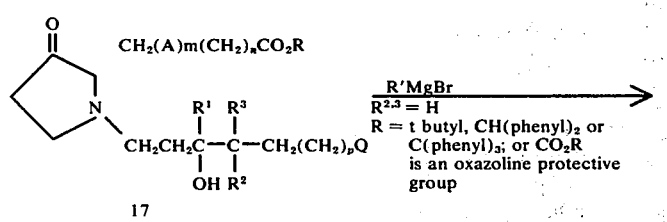

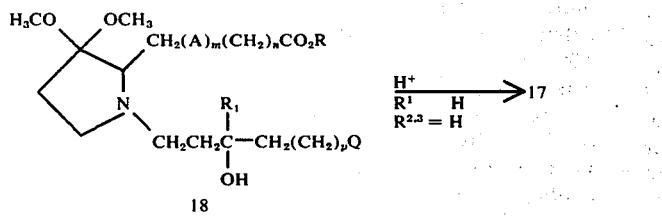

B. The 2,4pyrrolidindiones can be made by the following general synthetic sequence.

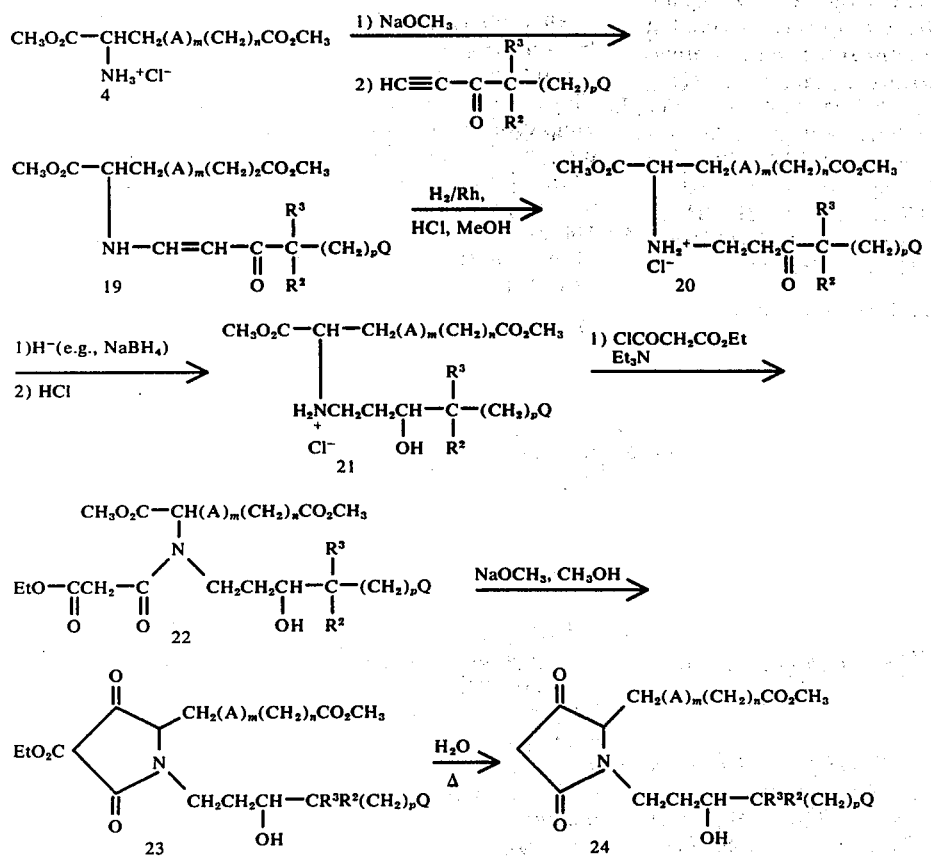

Likewise by similar, conventional organic reactions the intermediates indicated above can be converted to the other 2,4-pyrrolidindiones included in the general formula.

SPECIFIC EMBODIMENTS OF THE INVENTION

In the following illustrative examples all parts are by weight and all temperatures are Centigrade unless otherwise stated.

EXAMPLE 1

A. Triethyl 1-Acetamido-1,1,7-heptanetricarboxylate

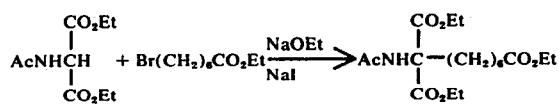

In a dried flask was dissolved 23.0 g (1.0 g atom) of sodium and 600 ml. of ethanol dried by the method of R. H. Manski, J. Am. Chem. Soc., 53, 1106 (1931). To the solution of sodium ethoxide, under nitrogen, was added 217 g (1.0 mole) of dry diethyl acetamidomalonate and 1.0 g of dry sodium iodide. The resulting solution was heated at reflux while 249 g (1.05 mole) of ethyl 7-bromoheptanoate was added dropwise over a period of 1.5–2 hrs. After addition was completed, the reaction mixture was heated at reflux for 20–24 hrs. By the end of this time a drop of the reaction mixture applied to moist pH paper indicated pH 6–7. The reaction mixture was cooled to room temperature, mixed with 2 liters of water and extracted with ether twice. The combined organic layers were washed with water twice and then with saturated sodium chloride, dried over MgSO$_4$ and evaporated under reduced pressure. The final stage of the evaporation was carried out at 70°–80° to remove last traces of solvent. The remaining oil, which weighed about 363 g, was distilled through a wiped-film molecular still (Rota-Film Molecular Still, All-Starr Scientific Equipment Supply Co., Pompano Beach, Fla.). A foreshot (about 45 g) was collected at about 100°/.01–.005 mm and discarded. Pure triethyl-1-acetamido-1,1,7-heptanetricarboxylate, about 316 g (85%), was then collected at 240°–250°/.005 mm. For other samples prepared similarly: HRMS Calcd for C$_{18}$H$_{31}$NO$_7$ m/e 373.2099, measured 373.2078; pmr (CDCl$_3$, TMS) δ1.25 (t, 9H, ethyl CH CH$_3$'s), 2.03 (s, 3H, COCH$_3$), 4.2 (q, 6H, OCH$_2$), 6.95 (s, 1H, NH); ir (neat) 3480 (NH), 1735 (—CO$_2$—), 1680 (CONH), 1500, 1470, 11450, 1375, 1210 (OC$_2$H$_5$) cm$^{-1}$.

B. 2-Aminoazaleic Acid Hydrochloride

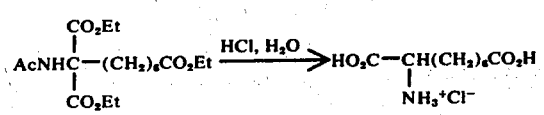

A mixture of 100 g of the triester (from A), 100 ml of concentrated hydrochloric acid, and 321 ml of water was heated at reflux temperature for 24 hrs. The cooled reaction mixture was extracted with ether and the ether was discarded. The aqueous layer was evaporated to dryness on a rotating evaporator, finally at 70°. The solid residue was taken up in 120 ml of methanol, 120 ml of benzene was added, and the solution was evaporated to dryness. The remaining solid was dried in a vacuum oven at 90° for at least 2.5 hrs. This dry solid was taken up in 75 ml of hot methanol, and 500 ml of ether was added dropwise to the cooled solution with stirring. This gave 57.5 g (90%) of white 2-aminoazaleic acid hydrochloride, m.p., about 204°–210°.

C. 2-Aminoazaleic Acid Dimethyl Ester Hydrochloride

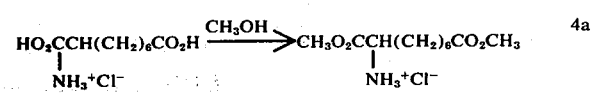

Into a refluxing solution of 13.0 g of the diacid hydrochloride (from B) in 250 ml of methanol was bubbled HCl gas for 15 min. The reaction mixture was heated at reflux temperature for an additional 1.5 hrs and then allowed to stand at room temperature over night. The solution was evaporated to dryness in vacuo and then 100 ml of fresh methanol was added and the solution was re-evaporated to give a waxy, white solid that was triturated with ether and collected by filtration. This solid was dissolved in 15 ml of methanol and precipitated by dropwise addition of 100 cc of ether with cooling, giving 8.48 g of the diester hydrochloride, m.p., 111°–115°; IR (KBr) 3.31, 3.80, 3.92, 5.15, 6.28, 5.76, 8.28μ; pmr (CDCl$_3$, TMS) δ 8.83 (broad, 3H, NH$_3^+$), 3.85 (s, 3H, OCH$_3$), 3.68 (s, 3H, OCH$_3$), etc; Anal. Calcd, for C$_{11}$H$_{22}$NO$_4$Cl: C, 49.34; H, 8.28; N, 5.23; C, 49.14; H, 8.27; N, 5.14.

Alternatively the diacid hydrochloride (from B) can be converted to the dimethyl ester by adding SOCl$_2$ to a solution of the diacid hydrochloride in methanol. Thus, to a solution of 124.7 g (0.52 mole) of the acid in 500 cc of methanol cooled in an ice bath was added dropwise 79 cc (130 g, 1.09 moles) of thionyl chloride. After 24 hrs at room temperature the reaction mixture was evaporated and the residue was crystallized from 100 ml of methanol and 1.2 l of ether, giving 107 g (78% yield) of the diester hydrochloride, m.p., 113°–118°.

D. N(p-Phenylbenzoyl)2-aminoazaleic Acid Dimethyl Ester (4a)

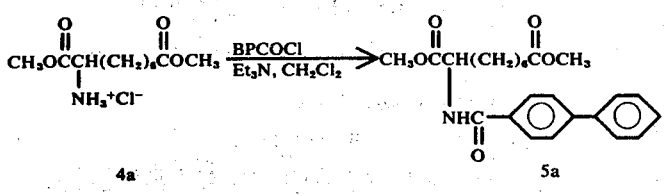

To a solution of 26.8 g (0.1 mole) of 2 aminoazaleic acid dimethyl ester hydrochloride and 23.8 g (0.11 mole) of biphenylcarbonyl chloride (recrystallized) in 0.5 l of methylene chloride under nitrogen was added 42 ml (30 g, 0.3 mole) of triethylamine dropwise over a period of about 1 hr with stirring and water-bath cooling. The reaction mixture was stirred at room temperature for 48 hrs and then 25 ml of water was added. The mixture was stirred vigorously for 1.5 hrs and then washed successively with water, 3 times with 5% HCl, 2 times with 5% NaHCO$_3$, and finally with saturated NaCl solution. Evaporation of the methylene chloride solution after it had been dried over MgSO$_4$ gave 38.7 g of a thick syrup which was dissolved rapidly in 100 ml of ether. From this solution precipitated a white or cream colored solid which was collected to two crops totaling 35.3 g (86%) and melted at 72°–73°. HRMS calcd'd for $C_{24}H_{29}NO_5$ 411.2044, measured 411.2058; pmr ($CDCl_3$, TMS δ 3.78 (s, 3H, $OCH_3$), 6.78 (d, 1H, NH), 4.83 (broad, 1H, CHN), 2.28 (t, 3H, $CH_2CO_2$), 7.2–8 (mult., 9H, aromatic).

E. 7[N-(p-Phenylbenzoyl)-3-ketopyrrolidin-2-yl]heptanoic Acid Methyl Ester (7a)

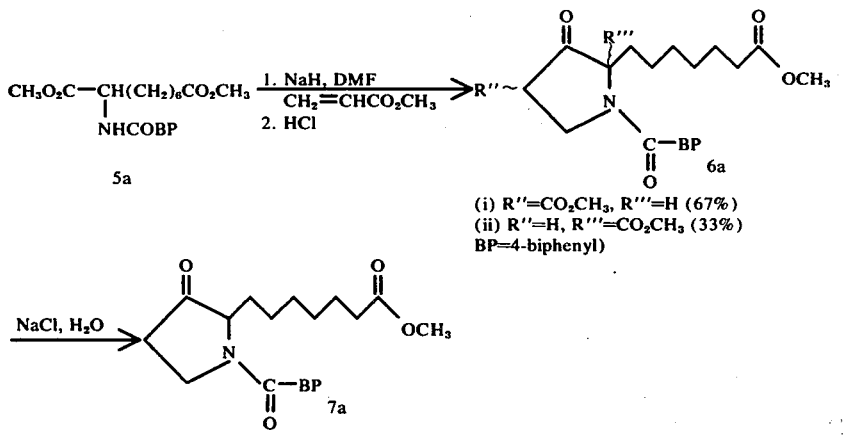

(i) R''=$CO_2CH_3$, R'''=H (67%)
(ii) R''=H, R'''=$CO_2CH_3$ (33%)
BP=4-biphenyl)

A mixture of 8.05 g (0.183 mole) of sodium hydride (54.5%) in Nujol was washed 3 times with petroleum ether under nitrogen. To the pure sodium hydride was added 100 ml of dried dimethylformamide and then a solution of 75.3 g (0.183 mole) of N(p-phenylbenzoyl)2-aminoazaleic acid dimethyl ester (5a) in 300 ml of dried dimethylformamide was added dropwise over 30 min with stirring and cooling, with a water-ice bath, to keep the temperature at 20°–25°. After the addition was completed, the mixture was stirred at 20°–25° for 30 min more, by the end of which time most of the sodium hydride had disappeared. Then 15.9 g (0.185 mole) of methyl acrylate was added over 10 min, during which time the temperature of the reaction mixture rose from 25 to 29°. After being stirred at room temperature for 24 hr, the reaction mixture was cooled to about 0° and a solution of 20 ml of conc. HCl in 100 ml of ice water was added with stirring all at once. The reaction mixture was poured into 1.5 l of water and extracted 3 times with ether. The combined ether extracts (550 ml) were washed 3 times with water, once with saturated NaCl, and dried over $Na_2SO_4$, giving 80 g of the crude β-keto esters 6a. In similar experiments one of the β-keto esters 6a (i) was isolated in about 67% yield as an oil by extraction into 0.2 N NaOH. It gave a positive test for enolic proton with $FeCl_3$ in water-methanol; field desorption mass spectroscopy showed a parent ion at 465 (calcd for $C_{27}H_{31}NO_6$; 465); conventional high resolution mass spectroscopy gave only parent ion corresponding to the decarbomethoxylation product $C_{25}H_{29}NO_4$; calcd 407.2095, measured 407.2111; $\lambda_{max}$ ($CHCl_3$) 1765 (cyclopentanone C=O), 1730 (ester CO), 1710 (amide), 1678, 1625, 15080, 1555; pmr agreed with the assigned β-keto ester structure, showing one $CO_2CH_3$ group as a doublet (cis and trans isomers).

A solution of 80 g of the crude β-keto esters 6a (i and ii) in 220 ml of dimethylsulfoxide with 12.8 g of sodium chloride and 6.6 ml of water was heated with stirring at 120° for 15 min and then the temperature was gradually raised over a period of 30 min to 140°, at which temperature it was held for 30 min. A total of about 2.6 l of gas was evolved (62% of theory). The mixture was cooled to room temperature, poured into 1.5 l of water, and extracted 4 times with chloroform. The chloroform solution was washed 3 times with water, twice with 5% $NaHCO_3$, once with saturated NaCl, dried over $MgSO_4$, and evaporated to give 80 g of a syrup. This syrup was rapidly dissolved in 125 ml of ether, from which there was collected in 3 crops a total of 44.7 g (65% yield) of light cream colored solid, 7a. An analytical sample of the pyrrolidone prepared similarly and recrystallized from methanol was colorless and had m.p. 90°–92°; Anal. calcd for $C_{25}H_{29}NO_4$: C, 73.68; H, 7.17; N, 3.44; Found C, 73.73; H, 7.35; N, 3.52; HRMS calcd 407.2119; Meas. 407.2085; $\lambda_{max}$ ($CHCl_3$) 3050, 2930, 2860, 1752 (C=O, strong, sharp) 1728 ($CO_2$—), 1625 (strong), 1610 (med.), 1581, 1558, 1520, 1488 (weak), 1418, 1238, 1180, 1000, 855 cm$^{-1}$; pmr ($CHCl_3$, TMS) δ 7.65 (s, 1H, aromatic), 7.58–7.33 (m, 1H, aromatic), 4.47 (m, 1H, COCHN), 3.87 (m, 2H, $CH_2N$), 2.55 (m, 2H, $CH_2CO$), 2.26 (t, 2H, $CH_2CO_2$), 3.63 (s, 3H, $CH_2CH_3$); a 220 MHz spectrum did not reduce the ring $CH_2$ multiplets to first order simplicity.

Both of these two reactions can be run in DMF without isolating the intermediate β-keto ester but yields are then lower.

F. d,l-7(Pyrrolidin-3-one-2-yl)heptanoic Acid Dimethyl Ketal Methyl Ester (9a)

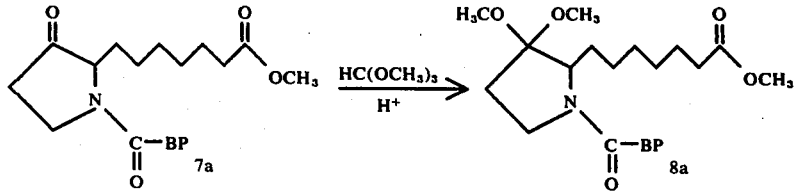

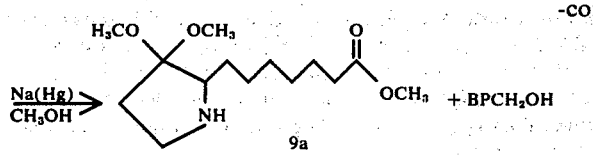

Ketal 8a was prepared by stirring 8.2 g (0.02 mole) of the pyrrolidone 7a, 35 ml of methanol, 10 ml of trimethyl orthoformate, and 0.5 ml of conc. $H_2SO_4$ in a stoppered flask at room temperature for 5.5 hr. Within a few min. the solution became clear. The solution was concentrated at about 30° under vacuum to about 20 cc and mixed with 100 cc ether. This ethereal solution was poured with stirring into 100 ml of cold, saturated $Na_2CO_3$ solution. The ether layer was drawn off and the aqueous phase washed with fresh ether. The combined ether layers were dried over $Na_2SO_4$ and evaporated, the final part of the evaporation being done under high vacuum over a weekend. This gave 8.48 g (98.9%) of ketal as a thick syrup; $\lambda_{max}$ (CHCl$_3$) 1735 cm$^{-1}$ (no keto C=O); pmr (CDCl$_3$, TMS) $\delta$ 3.63 (s, 3H, CO$_2$CH$_3$), 3.25 (s, 6H, OCH$_3$) (no methyl orthoformate detectable).

3% Sodium amalgam was prepared according to Org. Syn., 50, 50. It was washed with and stored under toluene with particular care being taken to avoid exposure of the amalgam to air (to minimize formation of NaOH). Forty grams of the amalgam, ground to approximately pea size, was placed in a three-necked flask equipped with a rubber system and a nitrogen inlet and outlet. The flask was evacuated 3 times and filled each time with dry nitrogen. The amalgam was stirred with 20 ml of dry methanol for 0.5 hr and the methanol removed with a hypodermic syringe. It was washed again with a second 20 ml portion of methanol for 5 min and this portion of methanol was removed. (Washing and complete exclusion of air is necessary for good yields). A solution of 2.13 g (.01 mole) of ketal 8a in 20 ml of methanol was injected into the amalgam and the mixture, cooled with a water bath at room temperature, was stirred for 5.5 hr. During this time the solid amalgam partly liquified. The methanolic solution was withdrawn and added to 20 ml of acetic acid. The resulting solution was evaporated nearly to dryness in a rotating evaporator and then partitioned between 50 ml of the ethyl acetate and 25 ml of an aqueous solution containing 5% $Na_2CO_3$ and 5% $NaHCO_3$ (pH 10). The aqueous phase was extracted with 50 ml more of fresh ethyl acetate, and the combined extracts washed once with a little saturated sodium chloride. The ethyl acetate solution was then extracted with three 25 ml portions of 0.2N HCl, each portion being run directly into 3.2 g of $Na_2CO_3$ and 20 ml of water. This aqueous mixture was quickly saturated with NaCl and extracted twice with a total of 100 cc of ethyl acetate. The ethyl acetate was dried over $Na_2SO_4$ and evaporated giving 0.898 g (66%) of d,l-amino ketal ester 9a as a nearly colorless, mobile liquid. This liquid was stored under nitrogen and in the cold (-25°). For a sample of this amino ketal prepared similarly: HRMS calcd for $C_{14}H_{27}NO_4$ 273.1938, m/e M$^+$ measured 273.1939; pmr (CDCl$_3$, TMS) $\delta$ 3.60 (s, 3H, CO$_2$CH$_3$), 3.20 (s, 3H, OCH$_3$), 3.13 (s, 3H, OCH$_3$).

G. Resolution of d,l-7-(Pyrrolidin-3-one-2-yl) heptanoic Acid Dimethyl Ketal Methyl Ester 9a

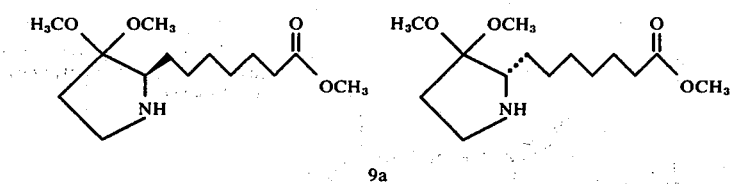

9a

To a solution of 1.42 g (5.2 mmoles) of d,l amine 9a in 12 ml of isopropanol was added with stirring 11.1 ml of a solution containing 0.070 g/ml of d (LEVO) tartaric acid in isopropanol. Within a few hours a crystalline solid appeared; usually no seeding was necessary. The mixture was cooled in an ice bath and the crystalline precipitate collected and rinsed successively with 2 ml of fresh isopropanol and ether, giving after drying at 50° under vacuum 1.067 g (98%) d-tartrate salt; the isopropanol mother liquor was set aside for isolation of the enantiomeric amine. The d-tartrate salt recrystallized from fresh isopropanol and dried was obtained as white plates, m.p. 137°–138°; $[\alpha]_{578}$ + 20°; $[\alpha]_{546}$ + 24°; $[\alpha]_{436}$ + 37°; $[\alpha]_{465}$ + 41°; $[\alpha]_{365}$ + 53° (C=1, H$_2$O). Pure, resolved d amine was obtained by partitioning 0.500 g of the d-tartrate between ethyl acetate and water buffered at pH 10 (5% Na$_2$CO$_3$, 5% NaHCO$_3$); the ethyl acetate was dried over Na$_2$SO$_4$ and evaporated giving the d amine 9a as a colorless, mobile liquid $[\alpha]_{578}$ + 50°; $[\alpha]_{546}$ + 56°; $[\alpha]_{436}$ + 93°; $[\alpha]_{405}$ + 110°; $[\alpha]_{365}$ + 142° (C=1, CHCl$_3$). The pmr spectrum of this d amine was consistent with the assigned structure. In CCl$_4$ in the presence of an optically active lanthanide shift reagent "Eu-Optishift II" the ketal methyl groups were moved strongly down field from their normal positions at 3.12 and 3.35 ppm. At a concentration of shift reagent that moved the peaks to 4.7 and 5.3 ppm respectively no l-isomer could be detected.

The mother liquor from crystallization of the d-tartrate.d-amine containing d-tartrate.l-amine was evaporated and the residue partitioned between ethyl acetate and 5% Na$_2$CO$_3$-5% NaHCO$_3$. The 0.817 g (3.0 mmole) of crude l-amine so obtained was dissolved in isopropanol and was treated with a solution of 0.45 g (3 mmoles) of l-(DEXTRO)tartaric acid in 18 ml of isopropanol. Within a few minutes white crystalline l-tartrate.l-amine salt appeared. After several hours the salt was collected by filtration, rinsed, and dried, giving 1.07 g (85%) of l-tartrate.l-amine; recrystallization from about 20 ml of fresh isopropanol gave white plates, m.p. 137°–138°; $[\alpha]_{578}$ −21°; $[\alpha]_{546}$ − 24°; $[\alpha]_{436}$ −39°, $[\alpha]_{465}$ −45°, $[\alpha]_{365}$ −55° (C=1, H$_2$O). Isolation of the free l-amine in the same manner as for the d amine gave a colorless, mobile liquid, $[\alpha]_{578} -52°$, $[\alpha]_{546} -60°$, $[\alpha]_{436} -96°$, $[\alpha]_{405} -112°$, $[\alpha]_{365} -143°$ C=1, CHCl₃). Its pmr spectrum in CCl₄ in the presence of optically-active lanthanide shift reagent showed no detectable amount of the d-isomer.

H.
7[N-(3-Hydroxy-n-octyl)pyrrolidin-3-one-2-yl]heptanoic Acid Methyl Ester 12a After 0.5 hr and again after 1.5 hr, 0.2 g portions of NaBH₄ were added. After a total reaction time of 3.5 hr the mixture was poured into 200 cc of water and extracted with 1:1 ethyl acetate-ether. This solution was extracted with two 25 ml portions of 0.5 N HCl (to remove amino ketal ester 9a and then with three 25 ml portions of 5N HCl. The 5N HCl extracts were combined, washed once with ether, and then basified with excess Na₂CO₃. Extraction of this basic solution with ethyl acetate twice gave in the latter 0.56 g of crude

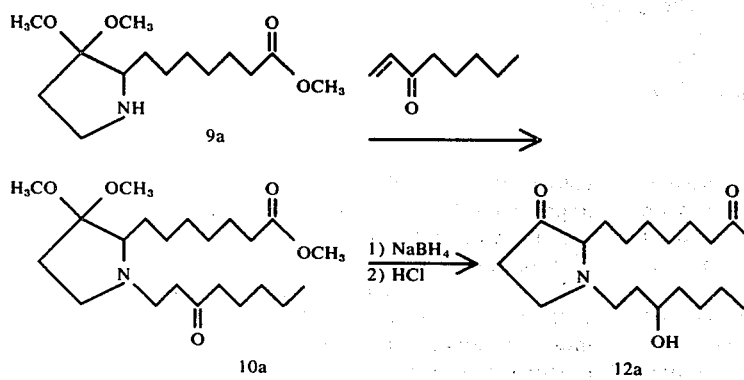

The following synthesis of 12a uses the total crude amino ketal ester 9a reduction with NaBH₄ and hydrolysis with HCl.

A solution of 4.0 g (9.3 mmoles) of 7[N-(p-phenyl-benzoyl)3-ketopyrrolidin-2-yl]heptanoic acid methyl ester 8a in 30 ml of methanol was reduced with 54 g of 3% Na(Hg) for 4 hr as described above. The supernatant methanolic solution was transferred to another flask under nitrogen and treated with 2.24 ml (2.3 g, 3 g mmoles) of glacial acetic acid. Then 0.5 g of NaHCO₃ and 2.0 ml (16 mmoles) of amyl vinyl ketone were added and the mixture was stirred at room temperature for about 65 hr. The mixture was cooled in an ice bath and 0.4 g of NaBH₄ (anal. grade) was added slowly.

product which was chromatographed on 30 g of basic, activity grade IV alumina. Elution with benzene and then 20% ether-benzene gave in the latter 0.244 g of pure product 12a ($R_f$=0.45, silica gel TLC, 1:1 CHCl₃-ether); $\lambda_{max}$ (smear) 1752 (pyrrolidone C=O), 1737 (ester CO) cm⁻¹; pmr (CDCl₃, TMS) δ 4.50 (broad; 1H, COCHN), 3.65 (s, 3H, OCH₃), 0.88 (t?, 3H, CCH₃); HRMS m/e calcd for C₂₀H₃₇NO₄ 355.270, measured 355.2714.

EXAMPLE 2

I. Resolved 7[N-(3-Hydroxy-n-octyl)pyrrolidin-3-one-2-yl]heptanoic Acid Methyl Ester

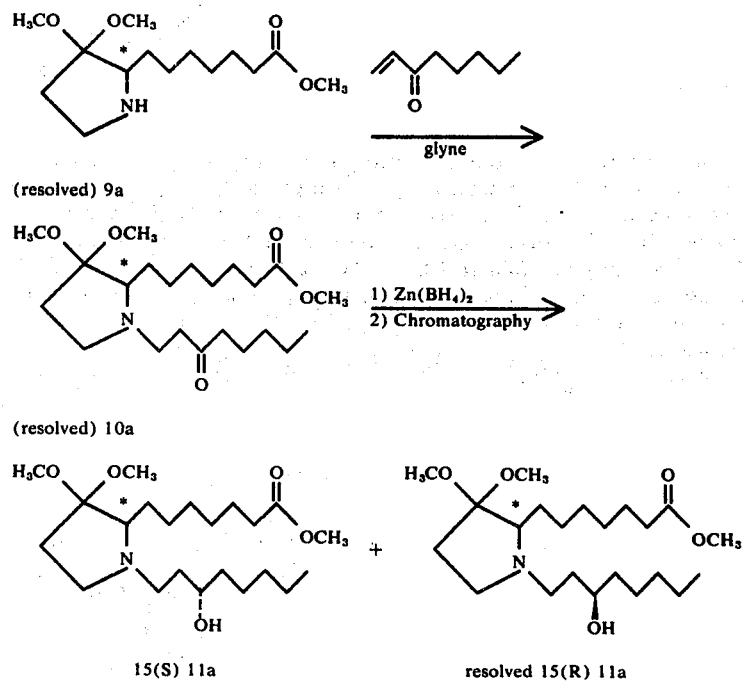

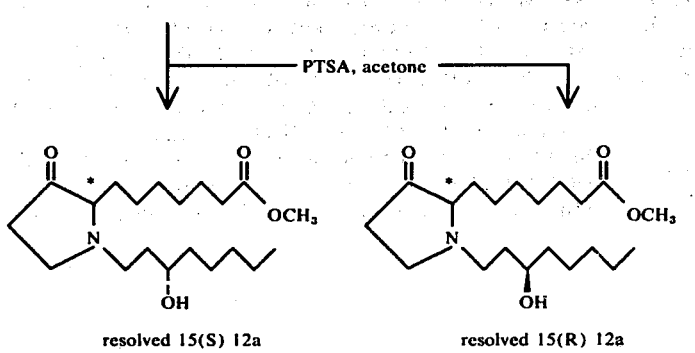

resolved 15(S) 12a      resolved 15(R) 12a (The asterisks in the above structures are intended to indicate that the compounds so marked have been resolved into a single enantiomer, but that the chiral atom near the asterisk is of unknown absolute configuration.)

A solution of 1.37 g (5.0 mmoles) of resolved (d) amine 9a (Example I) and 0.81 g (6.5 mmoles) of amyl vinyl ketone in 15 ml of dry ethylene glycol dimethylether was stirred under nitrogen at room temperature for 16 hr, and then to the solution of resolved ketone 10a so obtained was added 12 ml of 0.5M $Zn(BH_4)_2$ in ether. The mixture was heated at reflux temperature for 4 hr, cooled, poured into water, and extracted with ethyl acetate. Evaporation of the ethyl acetate gave 2.05 g of the crude 15(R) and 15(S) ols 11a which, being diastereomers, were separable by chromatography on Silicar CC-7 silica gel. Elution successively with benzene and then with 1:1 chloroform-benzene gave some reaction byproducts that were discarded; elution with 4:1 chloroform benzene gave one diastereomer 11a, and then elution with 2:1 chloroformethyl acetate gave the other diastereomer in approximately equal amounts. The chromatography was followed by thin layer chromatography on silica gel (2:1 acetone-benzene; iodine visualization).

The two diastereomeric ketals 11a can be hydrolyzed to the respective ketones 12a by treatment with a slight molar excess of p-toluenesulfonic acid.$H_2O$ in acetone at room temperature.

Use of the corresponding l amine 9a (Example D) in the example above in place of the d-amine gives the other set of diastereomers. Thus, all four optically active forms of 11a are obtained:

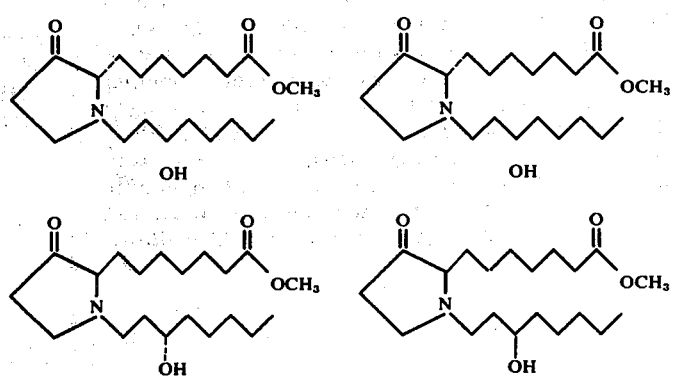

In all of the following examples the 3-pyrrolidones (e.g., 12) containing 2 chiral carbon atoms are isolated as mixture of 4 optical isomers; these 4 isomers can be separated, however, by use of optically active amines (9) and chromatography of the diastereomeric ketal alcohols 11 as just described.

EXAMPLE 3

J. 7[N-(3-Hydroxy-n-octyl)pyrrolidin-3-one-2yl] heptanoic Acid (13a) and its Hydrochloride (27a)

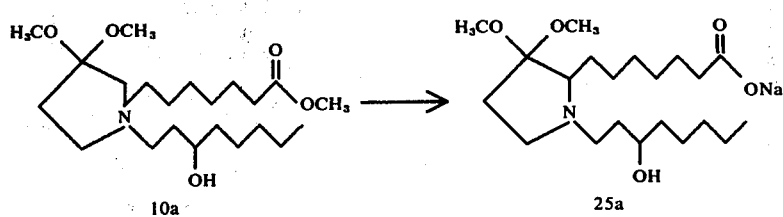

10a      25a

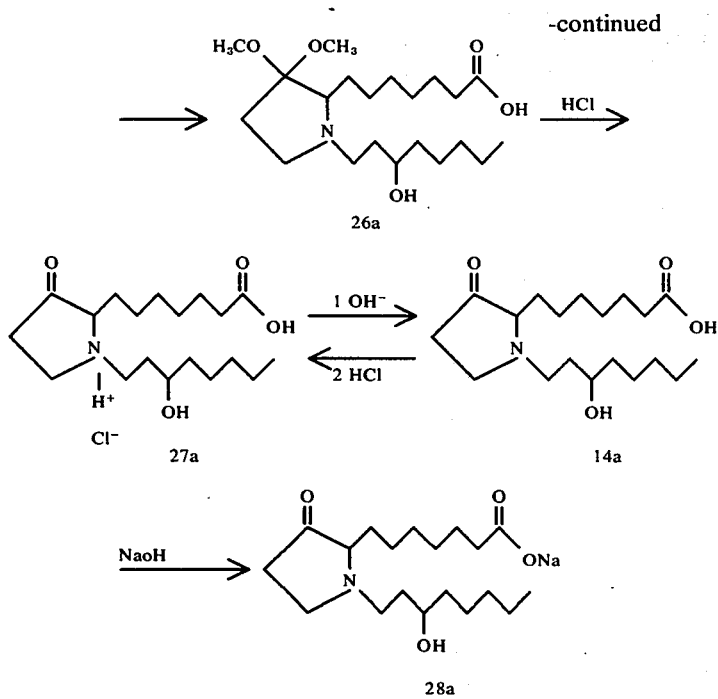

A solution of 4.17 g of crude d,l-ketal ester 10a, 22 ml of 1N NaOH, and 25 ml of methanol was heated at reflux for 1.5 hr, allowed to stand at room temperature overnight, and concentrated to about 20 cc on a rotating evaporator. Dilution with 80 cc of water and extraction twice with ether gave a clear aqueous solution of ketal sodium salt 25a. Acidification of this aqueous solution with aqueous HCl to pH 3, saturation of the aqueous mixture with NaCl, and extraction three times with chloroform gave, on evaporation of the organic extract, the ketal acid 26a. A mixture of 1.9 g of 26a, 25 ml of chloroform and 40 ml of 6N HCl was stirred vigorously under nitrogen for 2.3 hr at room temperature. The aqueous layer was drawn off and the chloroform layer and an insoluble third phase were extracted with two 20 ml portions of fresh 6N HCl. The combined HCl layers were washed once with $CHCl_3$ and filtered. The clear filtrate was adjusted to pH 3 with $K_2CO_3$ under a nitrogen atmosphere. The mixture was saturated with NaCl and extracted with two 150 ml portions of ethyl acetate. The ethyl acetate solution dried over $Na_2SO_4$ and evaporated, giving 0.73 g (43%) of the acid 13a. Addition of 1 equivalent of 1.0 N HCl to 13a gave an aqueous solution of hydrochloride 27a. Addition of one equivalent of aqueous NaOH gave an aqueous solution of the sodium salt 28a.

EXAMPLE 4

K.

7[N-(3-Hydroxy-n-decyl)pyrrolidin-3-one-2-yl]heptanoic Acid Methyl Ester (12b)

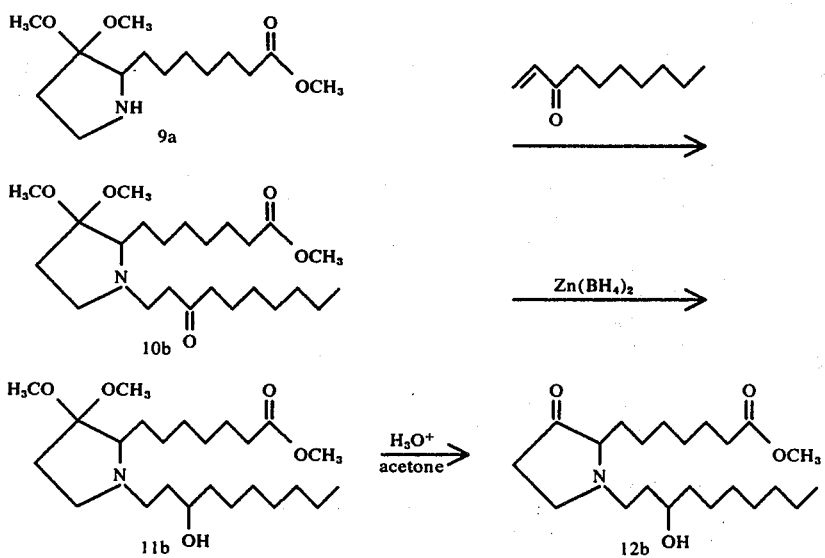

A solution of 1.53 g (4.76 mmoles) of amine 9a and 0.87 g (5.7 mmoles) of heptyl vinyl ketone (5.7 mmoles) in 20 ml of glyme was stirred under nitrogen for 18 hr at room temperature, giving a solution of the ketal ketone 10b. To this was added 12 ml of 0.5M Zn(BH$_4$)$_2$ in ether and the resulting solution was heated at reflux temperature for 3.5 hr. Cooling, pouring into water, extraction with ethyl acetate, and evaporation of the ethyl acetate gave 2.2 g (92%) of crude ketal alcohol 11b, $\lambda_{max}$ (smear) 3300, 2400, 1750 cm$^{-1}$. Chromatography of this crude hydroxy ketal 11b on 110 cc of Silicar CC-7 silica gel with mixtures of benzene- silica gel, 2:1 acetone-benzene, codeine) to be about 99% pure; HRMS calcd for m/e of M$^+$ for C$_{22}$H$_{41}$NO$_4$ 383.3033 and for M—OCH$_3$ 352.2860, measured 383.3046 and 352.2850.

EXAMPLE 5

L.

7[N-(3-Hydroxy-8-trifluoro-n-octyl)pyrrolidin-3-one-2yl] heptanoic Acid Methyl Ester (12c)

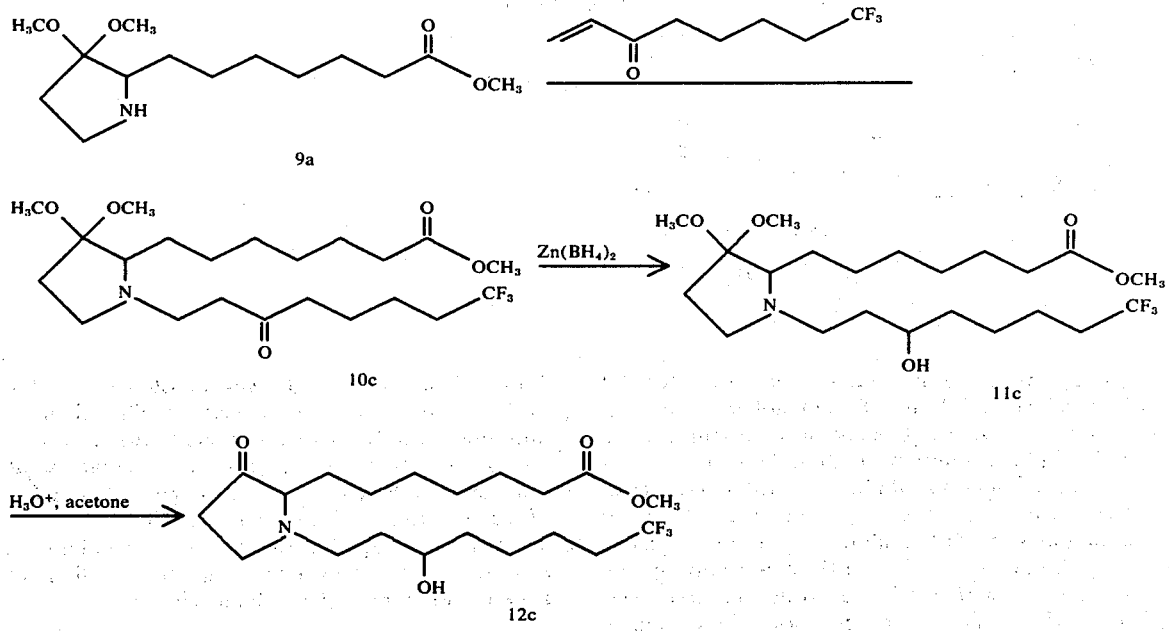

chloroform, chloroform and then chloroform-ethyl acetate gave amyl vinyl carbinol, then some of the hemiketal derived from 9a, and then two diastereomeric d,l-mixtures of ketal 11b. These diastereomeric mixtures on thin layer chromatography on silica gel (2:1 acetone benzene, iodine visualization) had R$_f$ values of 0.50 and 0.58 respectively; HRMS calcd m/e for M$^+$ of C$_{24}$H$_{47}$NO$_5$ 429.3452 and for M-CH$_3$ 414.3217, measured for the more mobile d,l-mixture 429.3471 and (M-CH$_3$) 414.3180; for the less mobile d, l-mixture measured 429.3475 and (M—CH$_3$) 414.3188. The pmr spectra of these ketal esters 11b were nearly identical and in agreement with the assigned structure. These ketal esters, obtained as colorless oils, were combined and weighed 1.52 g (75%).

These ketal esters (1.52 g) were converted to the corresponding ketones 12b in 50 ml of acetone in the presence of 1.3 g of p-toluenesulfonic acid. H$_2$O at room temperature for 21 hr. The reaction mixture was evaporated in vacuo and the residue partitioned between 75 ml of saturated NaHCO$_3$ and 150 ml of ethyl acetate. The ethyl acetate was washed with 25 ml of saturated NaHCO$_3$, dried, and evaporated, giving 1.21 g (89%) of the 3-pyrrolidones 12b as a colorless mobile liquid that was stored under nitrogen; $\lambda_{max}$ (smear) 3400 (broad) 1750, 1735; estimated by TLC (R$_f$=0.66

Amine 9a (1.50 g, 4.7 mmoles) was treated with 1.02 g (5.6 mmoles) of 5,5,5-trifluoroamyl vinyl ketone in glyme in a manner analogous to Example N, giving ketone 10c. This in turn was reduced with Zn(BH$_4$)$_2$ as in Example H, giving 2.3 g of crude alcohol 11c. Chromatography of 11c on 110 cc of Silicar CC-7 silica gel eluting with 4:1 CHCl$_3$-benzene and then with ethyl acetate gave 1.6 g pure 11c, characterized by its pmr spectrum. This purified 11c was treated with 1.6 g p-toluenesulfonic acid.$_2$O in 50 ml of acetone in a manner analogous to Example N giving 1.2 g of the 3-pyrrolidone 12c as a colorless oil which was stored under nitrogen: $\lambda_{max}$ (smear) 3350 (broad), 1748, 1732, 1300, 1130 cm$^{-1}$; pmr (CDCl$_3$, TMs) 3.67 (s, 3H's, CO$_2$CH$_3$), 4.92 ppm (s, 1H) etc,; TLC (2:1 acetone-benzene, iodine) indicated a single component, R$_f$=0.70; HRMS calcd for m/e of M$^+$ of C$_{20}$H$_{34}$F$_3$NO$_4$ 409.2438, M—CO 381.2484, M—(CH$_2$)$_4$CF$_3$ 284.1860, M—CO—CH$_2$CH(OH) (CH$_2$)$_4$CF$_3$ 98.0611, M—CO—(CH$_2$)$_6$CO$_2$CH$_3$ 238.1425; measured 409.2445, 381.2489, 284.1898, 98.0605, 238.1418 (with metastable at 148.7 from 381 → 238).

EXAMPLE 6

M. 7[N-(3-Hydroxy-5-phenyl-n-pentyl)pyrrolidin-3-one-2yl] heptanoic Acid Methyl Ester (12d)

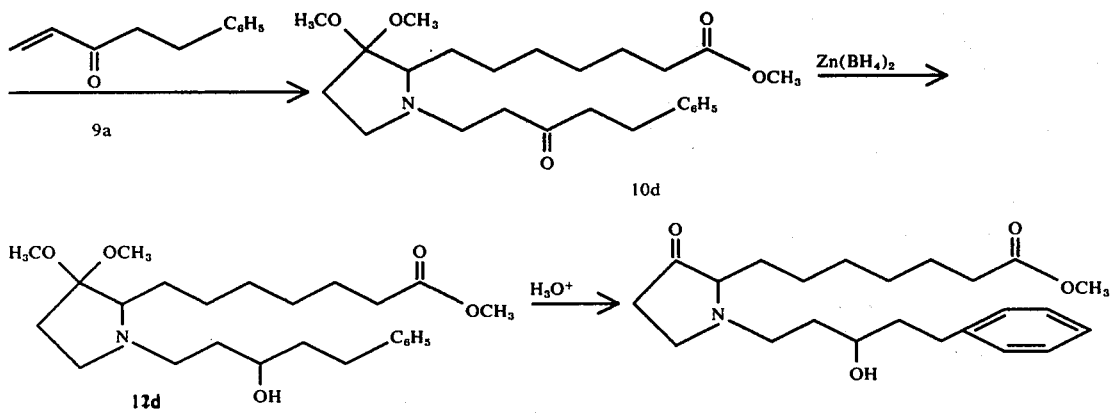

Amine 9a is treated with excess 2-phenylethyl vinyl ketone in glyme and then with $Zn(BH_4)_2$ in a manner analogous to the procedure described in Examples N and O giving successively ketone 10d and the alcohol 11d. Hydrolysis with p-toluenesulfonic acid in acetone affords the 3-pyrrolidinone 12d; pmr ($CDCl_3$, TMS $\delta$7.25 (5H), 3.65 (3H); $\lambda_{max}$ (neat) 1750, 1732, 1603, 710 cm$^{-1}$; HRMS m/e for M$^+$ of $C_{23}H_{39}NO_4$ Calcd. 389.2564, meas. 389.2588.

EXAMPLE 7

N. N-(3-Hydroxy-n-octyl)-2-aminoazaleic Acid Dimethyl Ester and its Hydrochloride (21a)

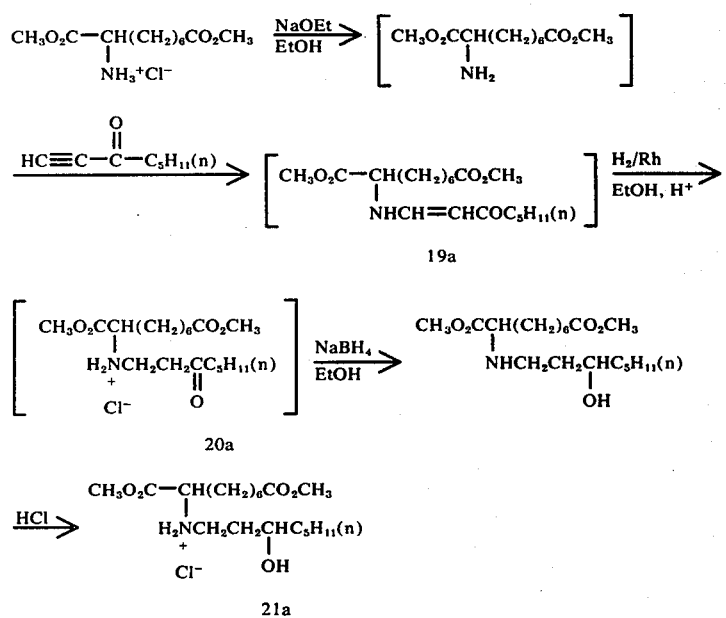

A solution of 0.758 g (32.95 mg atoms) of sodium in 25 ml of dry methanol was added dropwise to a solution of 9.3 g (34.6 mmoles) of the diester hydrochloride (from C) in 50 ml of methanol cooled in an ice bath. When the addition was completed 4.4 g (35.6 mmoles) of amyl ethynyl ketone was added and the reaction mixture was heated at reflux temperatures for 6 hrs under nitrogen.

To this mixture was added 9.5 ml of 4.35 M HCl in methanol and 3.0 g of 5% rhodium on carbon and the mixture was hydrogenated in a Parr shaker at about 40 psi for about 2 hrs, during which time about 60 mmoles of hydrogen were consumed. Filtration through Celite removed catalyst and NaCl. Evaporation of the light filtrate under reduced pressure gave an oil, the unstable amino ketone hydrochloride 20a. This was taken up in 100 ml of ethanol and the solution cooled in an ice bath and treated with 1.67 g (145 mmoles) of $NaBH_4$. After 10 min. the ice bath was removed and the mixture was stirred for 2 hrs at ambient temperature. This solution was poured in 350 ml of water and extracted with ether twice. The ether extract was washed once with 5% $NaHCO_3$ and then with three 100 ml portions of 0.3N (aqueous) HCl. The colorless HCl solution was washed once with ether and then basified with excess solid $NaHCO_3$ until effervescence ceased, and then about 1 g of $Na_2CO_3$ was added. The basic solution was then extracted with ether, which was washed with saturated NaCl, dried over $Na_2SO_4$, and evaporated, giving 6.65 g of a nearly colorless oil, the crude amino alcohol. The amino alcohol can be crystallized from petroleum ether and melts at about 40°–49° (mixture of 2 diasteromers); Anal. Calcd. for $C_{19}H_{37}NO_5$: C, 63.48; H, 10.37; N, 3.9°, Found for amino alcohol prepared similarly: C, 63.44; H, 10.15; N, 3.85. More conveniently, the crude amino alcohol was dissolved in 100 ml of dry ether and excess HCl gas was bubbled in, giving, after stirring overnight, 6.0 g (46%) of white solid amino alcohol hydrochloride 21a suitable for use in the next step. Amino alcohol hydrochloride 21a prepared similarly was recrystallized from ethyl acetate, giving pure material melting at 77°–85°; Anal. Calcd. for $C_{19}H_{38}NO_5$ Cl: C, 57.63; H, 9.67; N, 3.54; Found C, 57.35; H, 9.83; N, 3.48. The pmr spectra of the amino alcohol and its hydrochloride agreed well with their assigned structures.

O. N-(Ethoxycarbonylacetyl) N-(3-hydroxy-n-octyl)-2-aminoazaleic Acid Dimethyl Ester 22a

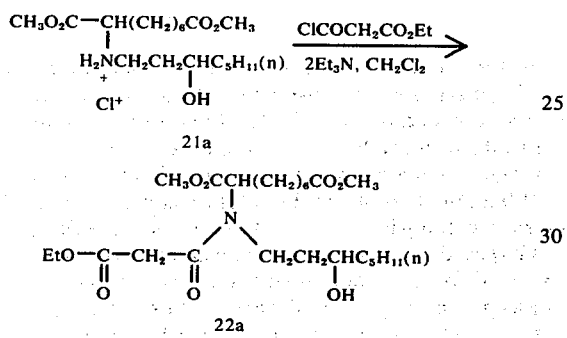

A solution of 3.96 g (10 mmoles) of aminoalcohol hydrochloride (prepared as in D) in 50 ml of methylene chloride was stirred and cooled in an ice bath under nitrogen while 3.6 ml (2.62 g, 26 mmoles) of triethylamine was added. A solution of 1.51 g (10 mmoles) of ethoxycarbonylacetyl chloride in 12 ml of methylene chloride was then added dropwise to the cooled reaction mixture. The reaction mixture was stirred overnight, allowing the ice to melt, and then diluted with 100 ml of methylene chloride. The solution was washed with three 30 ml portions of 2.5% HCl, once with 20 ml of 5% NaHCO₃, once with saturated NaCl solution, and dried over MgSO₄. Evaporation of the solvent gave 4.48 g (90%) of N(ethoxycarbonylacetyl) N-(3-hydroxy-n-octyl)-2-aminoazaleic acid dimethyl ester (22a), the structure of which was confirmed by pmr spectroscopy.

This compound can also be prepared from the free aminoalcohol (prepared as in D), in which case less triethylamine need be employed.

P. 7[N(3-hydroxy-n-octyl)-3-carboxy-2,4-dioxopyrrolidin-5yl] heptanoic Acid Dimethyl Ester (23a) and 7[N(3-hydroxy-n-octyl)-2,4-dioxopyrrolidin-5-yl]heptanoic Acid Methyl Ester (24a)

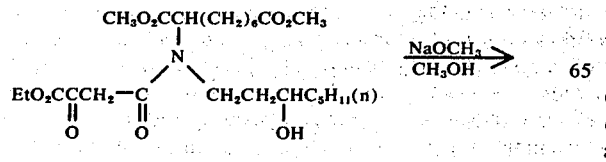

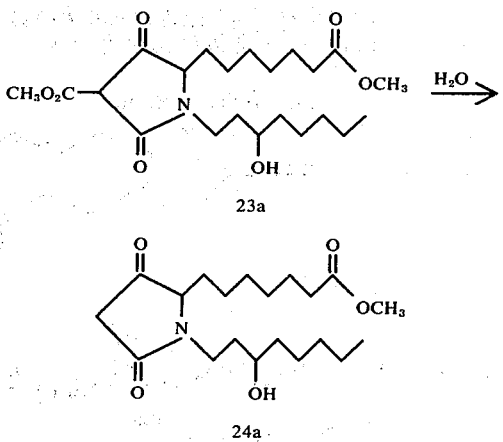

A solution of 436 mg (0.92 mmole) of the ethyl dimethyl ester 22a (prepared as in E) in 10 ml of methanol in which 24 mg of sodium had been dissolved was heated at reflux temperature for 2.5 hrs. The reaction mixture was cooled in ice, acidified with 0.5 ml of 2.0N HCl, and evaporated on a rotating evaporator at about 35° of 7[N(3-hydroxy-n-octyl)-3-carboxy-2,4-dioxopyrrolidin-5-yl]heptanoic acid dimethyl ester (23a). To this was added 15 ml of 0.1N HCl. The resulting mixture was heated at reflux for 1.0 hr, cooled, and extracted with ethyl acetate. The ethyl acetate layer was washed twice with 15-ml portions of 2.5% NaOH, and the combined aqueous extracts were acidified with conc. HCl. Extraction of the acidified aqueous solution with ethyl acetate and evaporation of the ethyl acetate solution after drying over Na₂SO₄ gave 156 mg (48%) of a colorless glass, 7[N(3-hydroxy-n-octyl)-3-carboxy-2,4-dioxopyrrolidin-5-yl]heptanoic acid methyl ester (24a); HRMS Calcd. for m/e of M⁺ of $C_{20}H_{35}NO_5$, 369.2513, measured 369.2537; pmr (COCl₃, TMS), δ 4.67 (s, 2H, COCH₂CO), 3.67 (s, 3H, OCH₃), etc.

3-Pyrrolidones

A. Synthesis of $XCH_2(A)_m(CH_2)_nCO_2CH_3$ where X is chloro, bromo, or iodo; A is CH=CH (cis), C≡C, o-, m-, or p-phenylene; m is 0 or 1; and n is 0–6.

Some of these esters or the corresponding acids are commercially available as the omega bromo or chloro compounds. The acids can be converted into the methyl esters by conventional methods. Although it is convenient to use the methyl or ethyl esters in the first step (1 → 2) of this process for making the 3-pyrrolidones of this invention, it makes little difference which ester is used since it is hydrolyzed to the corresponding acid in the following step (2 → 3). Available bromo- or chloro- esters can be converted into omega iodo esters by a Finkelstein halide interchange (cf., e.g., C. Buehler and D. Pearson, Survey of Organic Synthesis, Wiley-Interscience, N.Y., 1970, p. 339). The bromo esters or iodo esters are preferred for the reaction with diethyl acetamidomalonate, the bromo esters being used in the presence of sodium iodide which generates the more reactive iodo ester in situ.

The esters of this general formula in which m=o are either well known or easily prepared from well known ω-halo acids or esters by the processes described above.

The acids in which m=1 and A is phenylene, i.e., $XCH_2(C_6H_4)(CH_2)_nCO_2H$ are prepared by chloromethylation or bromomethylation of ω-anylalkanoic acids.

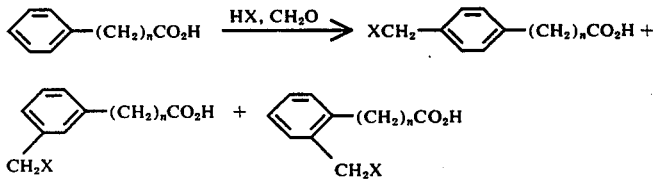

Mixtures of the o, m, and p-isomers are produced by these reactions [I. N. Nazarov et al., Bull. Acad. Sci. USSR, Div. Chem. Sci. 103 (1957)] and the preferred p-isomers are readily isolated by fractional crystallization. From the mother liquors of such crystallizations the corresponding ortho and meta isomers can be isolated by column chromatography or, in the case of their methyl ester derivatives, by preparative gas chromatography.

Chloromethylation is best carried out in the presence of zinc chloride (see G. A. Olah and W. S. Tolygyese in Olah, Friedel-Crafts and Related Reactions, Vol. II, part 2, Chapter XXI, Interscience, 1964). The benzyl chlorides are readily converted to the corresponding benzyl iodides by the action of NaI in acetone.

Although bromomethylation is reported to give less satisfactory yields than chlormethylation (*Organic Reactions*, Vol. I, Chap. 3, p. 72, Wiley and Sons, N.Y. 1942), in the case of the ω-phenylalkanoic acids, bromomethylation has been found more convenient. The benzyl bromides obtained are better N-alkylating agents than the corresponding benzyl chlorides, and they need not be converted to the corresponding relatively unstable benzyl iodides before reaction with amines of type 4. Better yields of bromomethylation products are obtained when the reactions are carried out in the absence of added zinc salts.

The ω-halomethyl alkanoic acids can be converted to their alkyl esters for example by reaction with diazoalkanes in ether or by Fischer (acid catalyzed) esterification with alcohols:

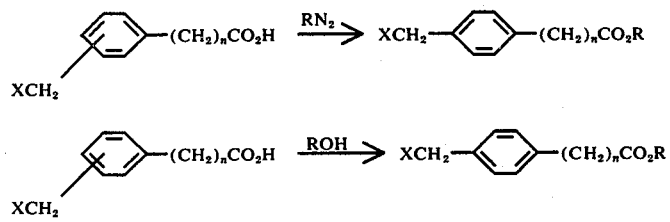

In the latter case yields are increased by using an excess of the alcohol and a drying agent, e.g., 3A or 4A molecular sieves, can be used.

Omega-halo carboxylic esters wherein m=1 and A is $C \equiv C$ are obtainable as follows. The acetylenic ester methyl 7-iodoheptynoate $XCH_2C \equiv C(CH_2)_nCO_2CH_3$; X=I, n=3, R=CH$_3$) has been prepared [Ferdinandi and Just, Can. J. Chem. 49, 1070 (1971)] and homologs can be prepared by similar processes. Starting with an ester of the first column below this gives the corresponding acetylenic ester of the second column, where the halogen is either bromo or iodo depending on whether the metal halide used in the process is LiBr or NaI.

| Ester | Acetylenic Ester |
|---|---|
| n=1 ethyl bromoacetate | ethyl 5-halopent-3-ynoate |
| n=2 ethyl 3-bromopropionate | propyl 6-halohex-4-ynoate |
| n=3 ethyl 4-bromobutyrate | methyl 7-halohept-5-ynoate |

For the synthesis of ethyl 4-halobut-2-ynoate, the case where n is 0, the following synthetic sequence can be used, starting with ethyl propionate.

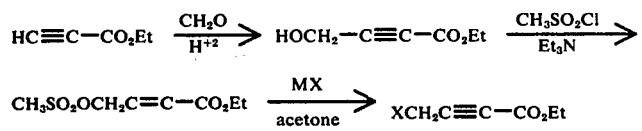

Omega halo carboxylic esters wherein m=1 and A is cis CH=CH are available by hydrogenation of the above described acetylenic esters (A is $C \equiv C$) over Lindlar catalyst or over Ni$_2$B catalyst. Lindlar catalyst [H. Lindlar, Helv. Chim. Acta 35, 446 (1952)] is palladium on calcium carbonate which has been deactivated by addition of lead acetate and quinoline. This catalyst is inactive toward hydrogenation of olefins and the hydrogenation of acetylenes over this material practically stops after absorption of one mole of hydrogen. Palladium on barium sulfate with synthetic quinoline is a similar catalyst but it is somewhat superior in reproductibility and ease of preparation [D. J. Cram and N. L. Allinger, J. Am. Chem. Soc. 78, 2518 (1956)]. Both catalysts give olefins of the cis configuration. Alternatively nickel boride catalyst (Ni$_2$B), especially that designated P-2 [H. C. Brown and C. A. Brown, JACS 85, 1005 (1963)] also effects catalytic reduction of the acetylenic compounds to cis olefins. J. Martel and E. Toromonoff in U.S. Pat. No. 3,806,540 (1974)

also describe the preparation of esters having the formula $XCH_2CH=CH-(CH_2)_n-CO_2Alk$ (cis) and $XCH_2C\equiv C(CH_2)_nCO_2Alk$, where Alk is alkyl of 1 to 7 carbon atoms.

Some of the omega-halo esters $XCH_2(A)_m(CH_2)n CO_2R''$ obtained as described above are listed in Table I, Column A. Most of these esters are, for the sake of brevity, listed as the preferred ethyl esters ($R''=C_2H_5$), but it should be understood that other esters such as methyl or isopropyl or tert-butyl can be employed in the synthesis described. For example, p-bromomethylpropionic acid (m.p., 133°–136°) is prepared by bromomethylation of β-phenylpropionic acid and this is turn is converted to the t-butyl ester d in Col. A by treatment with isobutylene in ether and sulfuric acid (cf., Org. Syn. Coll. Vol IV, 261).

B. Synthesis of the Salts of α-amino Dicarboxylic Acids 3 and their Esters 4

The omega-, bromo- or iodo- esters described in part A are treated with diethylacetamidomalonate in the presence of one equivalent of sodium alkoxide in refluxing alcohol, e.g., as in Example A. The triester 2 thus obtained can be purified by distillation but often the total crude product is satisfactory for the next step, which is hydrolysis-decarboxylation using concentrated aqueous mineral acid at reflux temperature as described in Example B, giving amino diacid salts 3. hydrochloric acid is preferred as the acid because it affords the same anion as that obtained in the subsequent esterification reaction with thionyl chloride. For example, ester d of Column A is converted by treatment with diethylacetamidomalonate and then with concentrated hydrochloric acid to

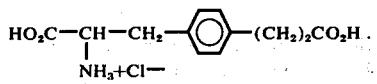

$$HO_2C-\underset{NH_3{}^+Cl^-}{CH}-CH_2-\text{⟨⟩}-(CH_2)_2CO_2H.$$

Although these amino diacid salts 3 can be esterified by conventional Fischer esterification (alcohol plus sulfuric acid) they are most conveniently converted to the amino diester salts 4 by dropwise addition of thionyl chloride to a lower alkanolic (preferably methanolic) solution) of the diacid amine hydrochloride 3. This affords only gaseous by-products and permits easy isolation of the amino diester salts 4.

For example, treatment of acid d of Col. B with methanol - $SOCl_2$ gives the p-phenylene diester amine hydrochloride, of Col. B, a white crystalline solid melting at about 190°–207°.

Column B of Table I lists some typical amino diester salts,

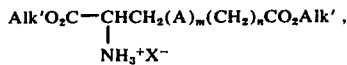

$$Alk'O_2C-\underset{NH_3{}^+X^-}{CHCH_2(A)_m(CH_2)_nCO_2Alk'},$$

thus obtained from the corresponding esters listed in Column A. For the sake of brevity most of these esters are the preferred amine dimethyl ester hydrochlorides, but it should be understood that by using other mineral acids for hydrolysis and other alcohols for esterification amines with other counter amines and esters of other low alcohols can be obtained.

C. Synthesis of N-(4-Biphenylcarbonyl)derivatives (5) of the Amino Esters 4.

Although amino esters 4 can be converted to conventional amides, e.g., to N-acetyl, N-benzoyl, or N-benzyloxycarbonyl amides, for use in the subsequent steps of this synthesis, the 4-biphenylcarbonyl amides are the preferred derivatives for this use because: (a) they usually afford crystalline products in this and in subsequent steps; (b) the 4-biphenylcarbonyl protecting group is easily and selectively removed later under mild conditions as described in Part C, below.

The diesters amine salts are conveniently treated as solutions in chloroform or methylene chloride with at least two equivalents of tertiary amine and with one equivalent of 4-biphenylcarbonyl chloride. The reaction can be carried out at room temperature for several days, or the reaction period can be shortened by heating the reaction mixture at reflux temperature. The amide thus obtained is isolated from the water-soluble tertiary amine salts by conventional means, but care must be taken to wash the crude amide 5 thoroughly with aqueous base to remove traces of p-phenylbenzoic acid which can interfere with the subsequent step.

Thus the diester amine salts of Col. B (Table I) are converted to the corresponding preferred 4-biphenylcarbonyl (BPCO) derivatives of Col. C (Table I).

D. Synthesis of the N-(p-Phenylbenzoyl)-3-pyrrolidin-2-yl Alkanoic Esters 6

As in Example E the N-(p-phenylbenzoyl) derivatives 5 are converted to the N-(p-phenylbenzoyl)3-pyrrolidone esters 6 by treatment of the amides 5 first with a strong base which is only weakly nucleophilic, e.g., NaH, potassium tert-butoxide, or lithium diisopropyl amide, or with metallic sodium in a non-protic solvent such as dimethyl formamide, tetrahydrofuran, glyme, or benzene. Generally warming to about 50–75° is required. The preferred base seems to be NaH and the preferred solvent is dimethyl formamide since the intermediate salt is quite sparingly soluble in less powerful solvents. The salt so obtained is then treated with an acrylate ester $CH_2=CHCO_2Alk$, where Alk is lower alkyl. Methyl acrylate is convenient to use. Addition of the acrylate ester to the salt (without isolating the salt) is generally accompanied by a mild exothermic reaction. The reaction can then be warmed to 35°–65° or allowed to stand without further warming for several hours to complete conversion of 5 to the cyclic products 6. The presence of the cyclic β-keto ester 6 thus obtained can be verified by the generation of a dark red or purple color on additon of a drop of the reaction mixture to ethanolic ferric chloride. Actually the cyclization of amides 5 to give pyrrolidines 6 affords two kinds of β-keto ester: one with an enolic proton (6i) and one without (6ii); the former gives a stable salt with the cation of the base employed. Although these 3-pyrrolidones (6i and 6ii) can be isolated, better yields of the decarboalkoxylated product pyrrolidones 7 are obtained when the total crude mixture of 6i and 6ii are used. Decarboalkoxylation can be accomplished by selectively hydrolyzing the β-keto esters 6 to the corresponding acids with dilute aqueous acid and then pyrolyzing the β-keto acid thus obtained. However, the preferred method is to subject the β-keto esters 6i and 6ii to decarboalkoxylation by a method described by A. P. Krapcho, et al. (Tetrahedron Letters, 1974, 1091) using water and NaCl. Dimethylsulfoxide or dimethylformamide work well as solvents and in fact the reaction mixture containing the pyrrolidones 6i and 6ii can be neutralized with aqueous HCl and the resulting mixture of NaCl, and $H_2O$ need only be heated to about 150°–160° to effect decarboalkoxylation of the β-keto ester. Generally, however, better yields of 7 are obtained when crude 6i and 6ii are separated from the dimethylformamide reaction medium and then treated with NaCl and H₂O as described in Example H. In this manner the pyrrolidone amides of Col. D (Table I) are obtained.

E. Protection of the Keto Groups of 3-Pyrrolidone Amides 7

The keto carbonyl groups of the 3-pyrrolidone amides 7 must be protected to prevent their reduction in the two subsequent steps: reduction with sodium amalgam and, later, reduction of the side chain keto groups (of 10) with borohydride. Although these 3-pyrrolidone carbonyl groups can be protected by a variety of different ways, e.g., as their ketals with 2,2-dimethylpropane-1,3-diol or as their thioketals with propane-1,3-diol, the most satisfactory derivatives are the dimethyl ketals. By using methylorthoformate in methanol with an acid catalyst such as sulfuric acid, these dimethyl ketals (8) can be formed in close to quantitative yield.

The 3-pyrrolidone amides of Col. D (Table I) under the conditions described in Example F give the dimethyl ketal amides of Col. E (Table I).

F. Removal of the 4-Biphenylcarbonyl Protecting Group from ketal Amides 8 to Give Ketal Amines 9.

Conventional methods of cleaving carboxamides to the corresponding amines are quite unsatisfactory for converting the ketal amides 8 to the ketal amines 9. For example, the action of NaOH/H₂O, or KOH/DMSO, or BF₃/MeOH at 110°, or Et₃O⁺BF₄⁻ followed by AcOH/H₂O or FSO₃CH₃ followed by NaHCO₃1H₂O on amides 8 gave little or none of the desired amine 9. It has been found, however, that treatment of 4-biphenylcarbonylamides with sodium amalgam in dry methanol affords the corresponding amines in good yields. An amalgam containing about 3% by weight of sodium is convenient to use, although amalgams containing as little as 1–2% Na or more than 3% Na can be used. The reaction is conveniently carried out in dry methanol, so that transesterification with the carbomethoxy groups of 8 or 9 do not become a problem. Other alcohols such as ethanol or isopropanol may be used as long as they are anhydrous. The reaction of sodium amalgam with the ketal amides 8 must be carried out in an atmosphere free of oxygen for good results. The reaction is generally carried out without external heating, although gentle cooling is sometimes desirable to control the mildly exothermic reaction. Usually about 4 – 6 hr reaction time is adequate. The ketal amines 9 are conveniently separated from the coproduced p-phenylbenzyl alcohol and traces of other by-product by extraction into aqueous 0.2N HCl. Basification of the aqueous HCl solution to pH 10 gives pure ketal amine 9 which can be extracted into ethyl acetate. The use of an HCl solution much stronger than 0.2N causes hydrolysis of the ketal; basification to a pH much less than 10 results in the loss of some ketal amine 8 in the aqueous phase because it is a very strong base; and basification to a much higher pH causes saponification of the ester group. Thus, following the general principles outlined above and exemplified by Example E, the ketal amides of Col. E (Table I) are converted by sodium amalgam to the ketal amines of Col. F (Table I).

Since ketal amines 9 possess a chiral carbon atom, they exist as d,l pairs. These can be resolved into pure d or pure l enantiomers by conventional resolution techniques, e.g., as described in Example G and S. W. Wiley in "Topics in Stereochemistry," N. L. Allinger and E. L. Eliel, et., Wiley & Sons, 1971, Vol. 6. One of the most useful resolving agents is tartaric acid, in its d-(LEVO) form or l-(DEXTRO) forms, and isopropanol is particularly useful as a solvent from which one of the diastereomeric tartrate salts precipitates pure and nearly quantitatively. Once the amine ketal 9 has been resolved, it in turn can be used as a "resolving agent" for the chiral center introduced later in the synthesis, as in Example I.

G. Reaction of Ketal Amines 9 with Vinyl Ketones to Give Ketones 10

The pure ketal amines 9 react quickly with vinyl ketones to give the ketal amine ketones 10. The reaction can be carried out without added solvent, or in the presence of tetrahydrofuran, ether, or glyme, the latter being the most convenient solvent. This procedure is exemplified by Example K. Or, total crude amine 10 resulting from sodium amalgam reduction and still in the presence of p-phenylbenzyl alcohol can be treated directly with the vinyl ketone to give crude ketal amino ketone 10 as in Example K.

The vinyl ketones used in this synthesis have the structure

and are prepared by two general processes: (1) by reaction of vinyl lithium (2 equivalents) with the appropriate carboxylic acid Q(CH₂)ₚCR R CO₂H (1 equivalent) in glyme according to the method described by J. C. Floyd in Tetrahedron Letters No. 33, pp. 2877-2878, 1974; or (2) by oxidation of the corresponding vinyl carbinols

which in turn are prepared by reaction of acrolein with suitable Grignard reagents. In either case the crude vinyl ketone is purified by distillation and stored in the presence of a trace of a polymerization inhibitor such as p-methoxyphenol (0.2% by wt.)

In particular, when R² and R³ are H and Q is H or CH₃ these vinyl ketones are as follows:

p=0 methyl vinyl ketones (Q=H) p=3 amyl vinyl ketone (Q=CH₃)

p=0 ethyl vinyl ketone (Q=CH₃) p=4 hexyl vinyl ketone (Q=CH₃)

p=1 propyl vinyl ketone (Q=CH₃) p=5 heptyl vinyl ketone (Q=CH₃)

p=2 butyl vinyl ketone (Q=CH₃) p=6 octyl vinyl ketone (Q=CH₃)

The first two ketones are commercially available; the others are readily prepared by oxidation of the corresponding carbinols. These oxidations can be carried out using CrO₃, H₂O, and sulfuric acid in acetone [K. Bowden, et al., *J. Chem. Soc.* 39 (1946)] or aqueous chromic acid/ether [H. C. Brown, *J. Org. Chem.* 36, 387 (1971)].

These vinyl ketones and those of the preceeding formula where R³ and R² are CH₃ or ethyl, p=0–6, and Q is H, CH$_3$, CF$_2$CH$_3$, CF$_3$, phenyl, or phenyl substituted with halo, methoxy, or lower alkyl are prepared by a sequence of reactions represented by the following equations where X is halogen (Cl, Br, or I):

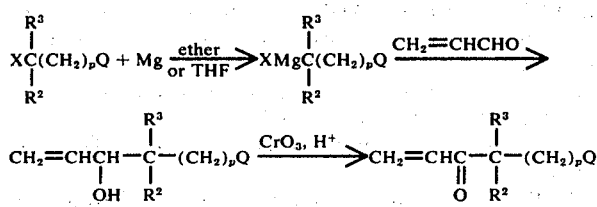

Thus the Grignard reagent derived from the halo compound XCR$^3$(R$^2$)(CH$_2$)$_p$Q is treated with acrolein to give a carbinol that on oxidation gives the vinyl ketone. The starting halo compounds are either known or available by conventional synthetic methods. Some typical syntheses of XCR$^3$(R$^2$)—(CH$_2$)$_p$Q are:

Br(CH$_2$)$_7$CF$_3$ — from reaction of Br(CH$_2$)$_7$CO$_2$H and SF$_4$. (see G. A. Boswell, Jr., W. C. Ripka, R. M. Scribner and C. W. Tullock, *Organic Reactions*, Vol. 21, W. G. Dauben, Editor, John Wiley and Sons, Inc., 1974).

Br(CH$_3$)$_2$(CH$_2$)$_5$CH$_3$ —from reaction of HBr with 2-methyl 2-heptanol.

I(CH$_2$)$_6$CF$_3$ — from reaction of I(CH$_2$)$_6$CO$_2$H and SF$_4$. (see G. A. Boswell, Jr., et al., loc. cit.)

ClC(CH$_3$)$_2$(CH$_2$)$_3$CF$_3$ from reaction of the Grignard reagent derived from CF$_3$(CH$_2$)$_3$Br with acetone followed by reaction of the resulting tertiary carbinol with HCl.

ICH(CH$_3$)(CH$_2$)$_2$CF$_2$CH$_3$ — from the reaction of 4-chloro-2-butanone with SF$_4$ to give 2,2-difluoro-4-chlorobutanone, followed by reaction of the Grignard reagent of the latter with acetaldehyde and conversion of the resulting secondary alcohol to the mesylate; treatment of the mesylate with sodium iodide in acetone gives the difluoroalkyl iodide.

BrCH(CH$_3$)(CH$_2$)$_3$ — from the action of carbon tetrabromide and triphenylphosphine on 2-pentanol.

ClC(C$_2$H$_5$)$_2$CH$_2$CH$_3$ — from the action of HCl on triethylcarbinol.

BrCH(CH$_3$)(CH$_2$)$_3$—C$_6$H$_4$—OCH$_3$(m) — from the reaction of the Grignard reagent from 3(m-methoxyphenyl-1-bromopropane with acetaldehyde followed by action of PBr$_3$ on the secondary alcohol thus obtained.

Br(CH$_2$)$_3$—C$_6$H$_4$—iC$_3$H$_7$(p) — from p-isopropyl dihydrocinnamic acid which is reduced with lithium aluminum hydride to 3-(p-isopropylphenyl)-1-propanol which in turn is treated with PBr$_3$.

The vinyl ketones CH$_2$=CHCOCR$^2$R$^3$(CH$_2$)$_p$Q where R$^3$ and R$^2$ include fluorine are prepared by two alternate methods: by reaction of the appropriate fluoroacyl chloride with ethylene followed by dehydrochlorination (method 1) or by reaction of the appropriate fluoroaldehyde with vinyl lithium followed by oxidation of the resulting carbinol to the ketone (method 2).

Method 1

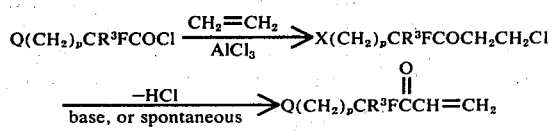

where R$^3$ is H, CH$_3$, or ethyl

The synthesis of alkyl vinyl ketones by this kind of process is well known to take place in the presence of aluminum chloride, stannic chloride, or zinc chloride. The β-chloroketone addition product readily loses HCl either spontaneously or on mild alkaline treatment [Catch et al., J. Chem Soc., 278 (1948); Colonge and Mostafavi, Bull. Soc. Chim. France, 6 (5), 341 (1939)]. The fluoroacids from which the acylchlorides are prepared are either reported in the literature or easily prepared by methods analogous to those described for the synthesis of closely-related fluoroacids. Several general methods of preparing α-fluoroacids are known [E. L. M. Patteson, et al., Can. J. Chem., 43, 1700 (1965); E. Elkirk, et al., Compt. Rend. Ser C, 262 (9), 763 (1966); E. Elkirk, Bull. Soc. Chem. France, 2254 (1964)]. These acids are in turn smoothly converted to the corresponding acyl chlorides (for use in the Friedel-Crafts addition to ethylene) by the action of well-known reagents such as SOCl$_2$ or PCl$_5$ (see for example, Buehler and Pearson, "Survey of Organic Syntheses," Wiley-Interscience, 1970, Chap. 15).

α,α-Difluoropropionic acid and α,α-difluorobutyric acid are examples of known α,α-difluoroalkanoic acids. The α,α-difluoro alkanoic acids can be made from reaction of sulfur tetrafluoride with the appropriate α-ketoalkanoic acid or the ester. If the reaction is carried out under mild conditions, e.g., at about 10° in CH$_2$Cl$_2$ solvent in the presence of HF catalyst, the keto group of the α-ketoalkanoic acid is converted to a gem-difluoro group while the carboxylic acid group, and to a lesser extent the ester group, is converted to an acyl fluoride group. Hydrolysis of the α,α-difluoroacyl fluoride and/or the α,α-difluoroalkanoic ester, gives the α,α-difluoroalkanoic acid.

Using method 1 the acids of column I are converted through their acid chlorides to the vinyl ketones of column II.

| Column I | Column II |
| --- | --- |
| n-C$_5$H$_{11}$CF$_2$CO$_2$H | n-C$_5$H$_{11}$CF$_2$COCH=CH$_2$ |
| n-C$_4$H$_9$CF(CH$_3$)CO$_2$H | n-C$_4$H$_9$CF(CH$_3$)COCH=CH$_2$ |
| CF$_3$(CH$_2$)$_3$CHFCO$_2$H | CF$_3$(CH$_2$)$_3$CHFCOCH=CH$_2$ |
| CH$_3$CF$_2$CH$_2$CHFCO$_2$H | CH$_3$CF$_2$CH$_2$CHFCOCH=CH$_2$ |
| C$_2$H$_5$CF$_2$CO$_2$H | C$_2$H$_5$CF$_2$COCH=CH$_2$ |

-continued

| Column I | Column II |
|---|---|
|  | 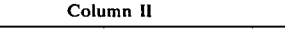 |
|  |  |

Method 2

This synthesis of fluoroalkyl vinyl ketones can be represented by the following equations.

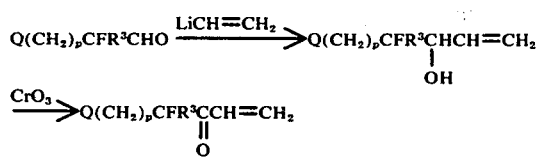

The starting fluoroaldehydes Q(CH$_2$)$_p$CFR$^4$CHO can be made by conventional methods of organic synthesis. For example, reduction of fluoroalkanoic acids with LiAlH$_4$ with NaAlH (OCH$_2$CH$_2$OCH$_3$)$_2$ provides the aldehydes (or their hydrates). Other methods for making α-fluoroaldehydes are known (e.g., J. Cantacuzine and D. Ricard, Bull. Soc. Chim. France, 1967 (5), 1507; F. L. M. Pattison, loc. cit.), and in some cases these methods are more convenient than reduction of the fluoroalkanoic acids.

Using the vinyl lithium method of method 2 the aldehydes of column III are converted in two steps to the vinyl ketones of column IV.

| Column III | Column IV |
|---|---|
| n-C$_6$H$_{13}$CHFCHO | C$_6$H$_{13}$CHFCCH=CH$_2$<br>‖<br>O |
| CH$_3$CH$_2$CF(Et)CHO | CH$_3$CH$_2$CF(Et)CCH=CH$_2$<br>‖<br>O |
| CF$_3$(CH$_2$)$_4$CHO | CF$_3$(CH$_2$)$_4$CCH=CH$_2$<br>‖<br>O |

Thus in the manner of Examples H, I, K, L or M the vinyl ketones prepared as described above and listed in Col. G (Table I) can be allowed to react with the corresponding ketal amines of Col. F (Table I) to produce the corresponding ketal amino ketones of Col. H (Table I).

H. Reduction of the Ketal Amino Ketones 10 to the Ketal Amino Alcohols 11.

The ketal amino ketones 10 are reduced with borohydride reducing agents to the corresponding ketal amino alcohols 11, for example, according to the procedures described in Examples H–I, K–M. The reductions are carried out either at room temperature for 10–48 hr or at higher temperatures, e.g. up to 80°; for shorter periods of time. Two precautions must be observed for best yields of the desired ketal amino alcohols: (1) the reduction reaction mixture should not be allowed to become strongly basic, for under these conditions the ketones 10 undergo reverse Michael condensation to afford the starting vinyl ketones and amines 9; (2) the reduction should not be carried out at temperatures as high as 70° for longer than about 6 hr for with longer reaction times the terminal carboalkoxy groups are reduced to the corresponding alcohols.

A preferred reducing agent is zinc borohydride, prepared as a solution in ether [W. J. Gensler, et al., J. Am. Chem. Soc., 82, 6074 (1960)], since its solutions are nearly neutral. A convenient solvent for the reductions is a mixture of ethylene glycol dimethyl ether ("glyme") and ether (approx. 3:1) since this solvent pair has a higher boiling point and greater solubilizing power than ether alone. When refluxing 1:1 ether-tetrahydrofuran was used as the reaction solvent for example a large amount of unchanged ketone was still present after 1 hr in the presence of a large excess of Zn(BH$_4$)$_2$.

Reduction of ketones 10 with Zn(BH$_4$)$_2$ (or with NaBH$_4$) gives close to equimolar amounts of the epimeric R- and S- alcohols 11. Thus if a d, l-mixture of ketal amine 9 is used to prepare ketone 10, close to equimolar amounts of each of the four optically active forms of the ketal amino alcohols 11 are obtained. These four structures can be specified as follows, where R$^1$=H and R=alkyl and the other symbols are as designated before.

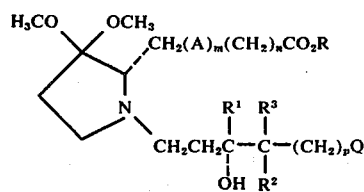

11A (8 nat., 15 nat.)

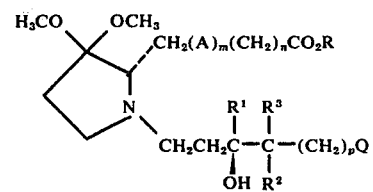

11B (8 nat., 15 epi.)

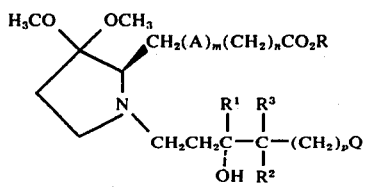

11C (8 epi., 15 nat.)

-continued

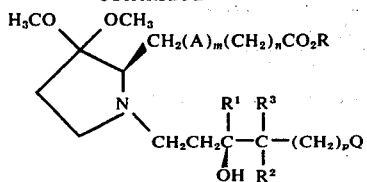

11D (8 epi., 15 epi.)

If, instead, resolved ketal amine 9 (i.e., the dextrorotatory form d, or the levorotatory form 1) is converted to ketone 10 and this in turn is reduced, only 2 products 11A and 11B, or 11C and 11D are obtained and these being diastereomers are separable by chromatography. Each pair of products will be composed of one 15R and one 15-S isomer, the former being characterized as epimeric to the natural prostaglandin configuration and the latter being characterized as the same as the natural prostaglandin configuration. One of these four compounds (11D) being epimeric at C-8 and at C-15 with the natural prostaglandin configuration can be considered the mirror image of the 12-azaprostanoid (11A) having natural configurations at C-8 and C-15.

By using hindered borohydride reducing agents, especially the bulky trialkylborohydrides such as lithium perhydro-9b-borophenalylhydride or potassium tri-sec-butylborohydride, reduction of the ketone 10 proceeds in a stereo-selective manner to give alcohols 11 enriched in either the 15R or 15-S isomer depending on the ketone and reducing agent involved.

Thus by procedures analogous to those described in Examples H, I, K, L and M, the ketal amino ketones of Col. H (Table I) are reduced by borohydride reducing agents to give the corresponding ketal amino alcohols of Col. I (Table I). In these tables and in the text where all the chemical bonds to chiral carbon atoms are represented by solid lines (rather than by broken lines or wedges) it is our intention to indicate that the chiral carbon atoms of such compounds exist either in both absolute configurations, that is as mixtures of two d, l forms, or that one or both chiral carbon atoms exist in one absolute configuration, depending on whether optical resolutions have been carried out as described above. That is, solid lines to chiral carbon atoms in themselves should be regarded as non-committal with respect to configuration.

I. Conversion of Ketals 11 to Ketones 12

Treatment of ketals 11 with strong acids such as aqueous mineral acids at concentrations of about 5N or greater hydrolyzes them to ketones 12. Preferably, however, these ketals are converted to ketones 12 by the action of 1.1 or more equivalents of p-toluenesulfonic acid in acetone at room temperature for at least 6 hr. These conditions in which acetone apparently plays a role in a trans-ketalization reaction, afford better yields of ketones 12 than does mineral acid hydrolysis. Thus, as described in Example K the ketals of Col. I (Table I) are converted to the 3-pyrrolidones of Col. J (Table I).

J. Other Esters of 12

Other esters of the 3-pyrrolidones 12 can be prepared by conventional synthetic methods applied to several different intermediates in the synthetic scheme described above. Saponification of the 3-pyrrolidone amides 7 with one equivalent of sodium hydroxide in refluxing aqueous methanol followed by acidification with mineral acid affords the generally crystalline carboxylic acids

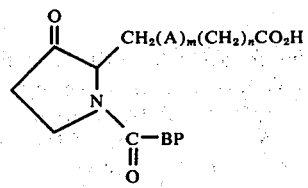

For example, where m=0 and n=5, the acid is obtained as a white crystalline solid, m.p., 102°–3°. These acids are converted into the esters

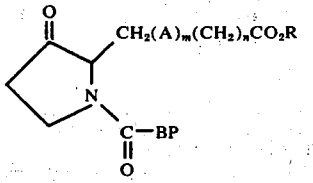

where R is alkyl or cycloalkyl of up to 12 carbon atoms by conventional methods (e.g., as in Buehler and Pearson, loc. cit, Chap. 14) and these esters can be carried through the synthesis described for the methyl esters 7 to give finally the esters analogous to methyl esters 12, i.e.,

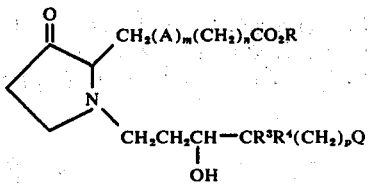

where R is as defined above.

The ketal amides 8 can be used as precursors to other esters also. Ketal amides 8 are saponified with aqueous sodium hydroxide in methanol and then acidified with a slight excess of 0.2N HCl to give the acids 25, which in turn can be converted

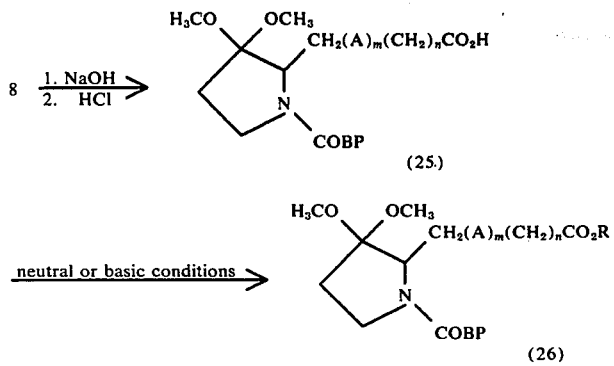

to esters 26 under neutral or basic conditions (strongly acidic conditions hydrolyze the dimethyl ketal groups). For example, treatment of ketal acid 25 with diazoalkanes RN$_2$, or with alcohols in the presence of N,N¹-dicyclohexylcarbodiimide, or of the alkali metal, silver, or amine salts of 25 with alkyl halides, gives ketal esters 26. Thus by well known procedures (see for example E. Haslam, "Protection of Carboxyl Groups," Chap. 5 in "Protective Groups in Organic Chemistry," J. F. W. McOmie, ed., Plenum Press, N.Y., 1973) ketal esters 26 such as those listed in Col. K (Table I) can be prepared from the corresponding esters of Col. E (Table I). By carrying the esters of Col. K (Table I) through a synthetic sequence exactly analogous to that used for the esters of Col. E (Table I), using the corresponding vinyl ketones of Col. G (Table I), the esters of Col. L (Table I) are obtained.

K. Synthesis of the Tertiary Alcohols

The 3-pyrrolidones of this invention in which the carbon atom bearing the side chain hydroxyl groups also bear a methyl, ethyl, vinyl, or ethynyl group, i.e., the compounds

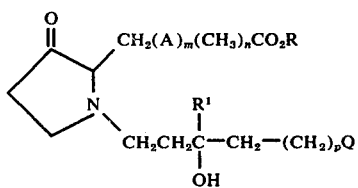

where R¹ is CH$_3$, C$_2$H$_5$, CH=CH$_2$, or C≡CH, are prepared by a series of reactions in which the key step is reaction of an organo metallic reagent R¹Z with ketone 27

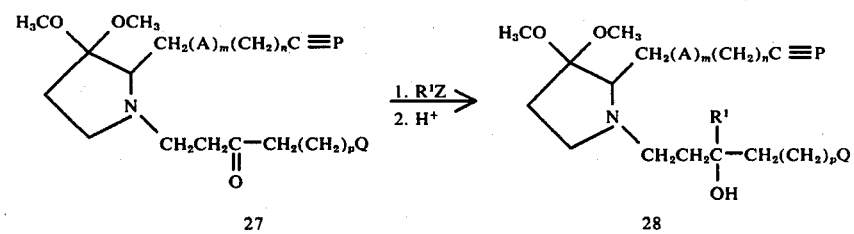

The group C≡P represents a carboxyl group protected from attack by the reagent R¹Z either as a hindered ester or as an oxazoline.

The organo metallic reagent R¹Z is typified by methylmagnesium iodide, ethylmagnesium bromide, vinyl lithium, and sodium acetylide. The hindered esters are typified by tertiary butyl, benzhydryl or trityl esters, i.e., —C≡P is —CO$_2$C(CH$_3$)$_3$, —CO$_2$CH(C$_6$H$_5$)$_2$, or —CO$_2$C(C$_6$H$_5$)$_3$. Dimethyloxazolines, in which —C≡P in 27 is the masked carboxyl group

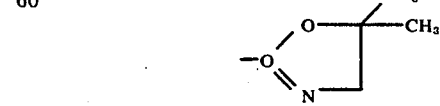

is especially useful for the purpose of this synthesis.
The synthesis of ketones 27 is represented as follows.

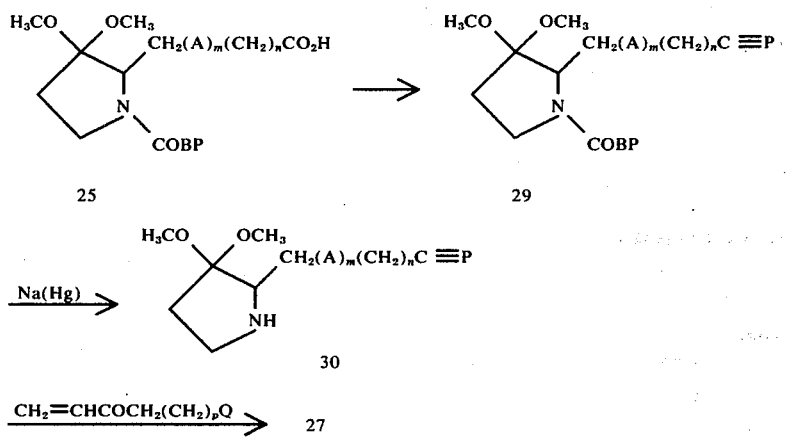

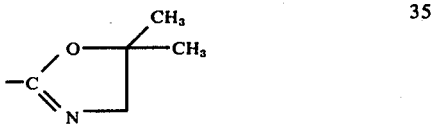

The acids 25 are protected as the above named hindered esters by well known general methods such as those described by E. Haslam, loc. cit. For example, reaction of acids with diphenyldiazomethane gives esters 28 where C≡P is $CO_2CH(C_6H_5)_2$. Acids 25, or the corresponding methyl or ethyl esters (26, R=$CH_3$ or $C_2H_5$), are converted directly into dimethyloxazolines by methods described by A. I. Meyers, et al. [e.g., J. Org. Chem. 39, 2787 (1974)]. For example acids 25 react with 2,2-dimethylaziridine in the presence of N,N'dicyclohexylcarbodiimide to afford the acylaziridines which in turn on very mild acid treatment (such as triethylammonium tosylate in $CH_2Cl_2$) afford the dimethyloxazalines 29 where

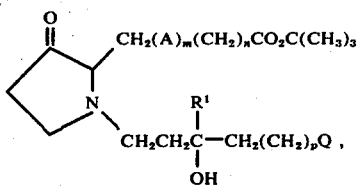

or ester 8 can be treated with the magnesium bromide salt of 2,2-dimethylaziridine to give the same intermediate acylaziridines.

Treatment of 29 with sodium amalgam gives the corresponding amines 30 in good yield. These amines are then treated directly with the vinyl ketones $CH_2$=$CHCOCCH_2$—$(CH_2)_pQ$ as described for example in Example 27 to give the ketones 27.

As stated above, ketones 27 are then treated with the organometallic reagents $R^1X$ to afford the tertiary alcohols 28. The reaction is carried out in tetrahydrofuran, glyme, or ether, or a mixture of these solvents using exactly one quivalent of the reagent $R^1X$. With the more reactive reagents such as vinyl lithium it is sometimes necessary to cool the reaction mixture to about −20° for good yields of the desired product but generally the reaction can be conducted at room temperature. After several hours the total crude product is neutralized with acetic acid and the tertiary alcohol 28 can be isolated by chromatography.

When a tertiary butyl ester group $CO_2tBu$ is used as the protecting group C≡P, the alcohol 28 can be treated with p-toluenesulfonic acid in acetone as described above in Section I giving the ketone-tertiary butyl esters

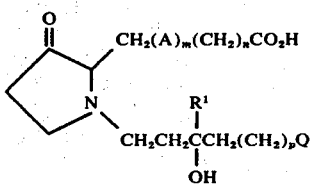

or alcohol 28 can be treated with mineral acid to afford the ketone acids 31 directly. Similarly, when benzhydryl or trityl groups are used on the protecting ester groups they can be removed from 28 with strong mineral acids, which also hydrolyze the dimethyl ketal group, affording the keto acids 31. The dimethyloxazalines 32 on treatment with aqueous mineral acid,

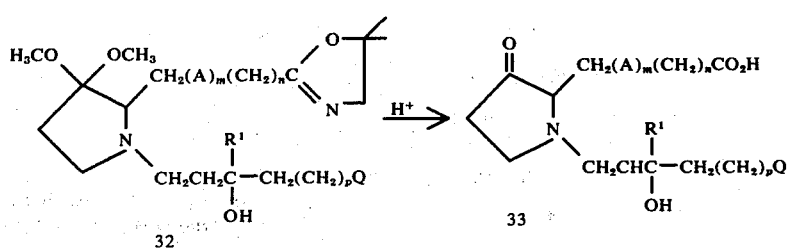

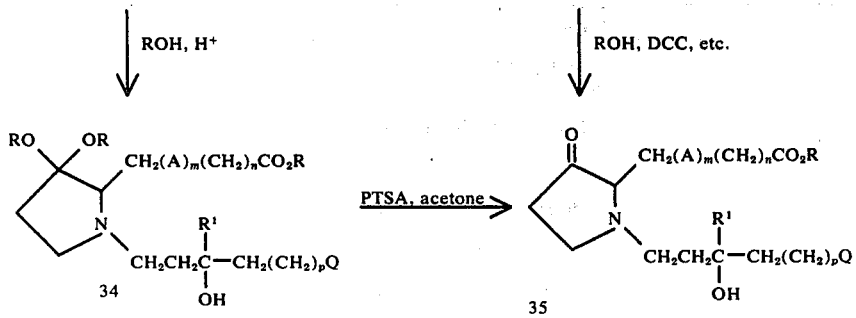

e.g., 3N HCl, afford the keto acids 33 directly. These dimethyloxazolines can also be treated with anhydrous alcohols containing mineral acid, e.g., 8% $H_2SO_4$, to afford the ketal esters 34; the latter can be hydrolyzed in the usual manner with p-toluenesulfonic acid in acetone to afford the keto esters 35. Keto acids 33 can also be converted to esters 35 by the conventional esterification methods referred to above, e.g., by the action of diazoalkanes $RN_2$ or by the action of the alcohols ROH in the presence of N,N'-dicyclohexyldicarbodiimide.

Thus by the sequence of reactions described above the ketal amides (26) of Col. E (Table I) or Col. K (Table I), or the corresponding carboxylic acids, are converted into the corresponding hindered esters or masked carboxyl group derivatives (29) of Col. M (Table I). By the action of sodium amalgam the corresponding protected ketal amines of Col. N (Table I) are produced, and the latter on treatment with the corresponding vinyl ketones of Col. O (Table I) afford the corresponding ketal amino ketones (27) of Col. P (Table I). Treatment of the ketal amino ketones of Col. P (Table I) with the corresponding organometallic reagent $R^1Z$ of Col. Q (Table I) as described above gives the corresponding tertiary alcohols of Col. R (Table I). Treatment of the tertiary butyl esters of Col. R (e.g., a) with p-toluenesulfonic acid in acetone as described previously gives the corresponding tertiary butyl ester ketones of Col. S (e.g., a). Or treatment of the benzhydryl ester of Col. R (i.e., b, f, i, and k) with a strong acid (e.g., HCl or HBr in $CH_3NO_2$, or with trifluoroacetic acid) followed by p-toluenesulfonic acid in acetone, gives the corresponding acids of Col. S (i.e., b, f), or the corresponding esters (i.e., i and k) by subsequent esterification of such acids are obtained. The trityl esters of Col. R (i.e., c and g) are likewise cleaved by strong acids to afford the corresponding carboxylic acids (E. Haslam, loc. cit.). These acids (33) can also be converted to esters 35 (Col. S, g) as described above. Or the oxazalines of Col. M (Table I) (d, j) can be converted successively as described above to the corresponding amines of Col. N (Table I) ketal amino ketones of Col. P (Table I) (by reaction with the corresponding vinyl ketones of O) (Table I), the tertiary alcohols of Col. R (Table I) (by reaction with the corresponding organometallic reagents of Col. Q (Table I), and finally by way of the ketal esters 34 by successive treatment with alcohol containing some mineral acid (e.g., 8% by wt. $H_2SO_4$) and then with p-toluenesulfonic acid in acetone to the tertiary alcohol esters 35 of Col. S/d, j(Table I).

L. Salts

Neutralization of the acids 36 where R=H (or 33) with one equivalent of base MOH or $MHCO_3$ where M is an alkali metal gives the corresponding alkali metal salts 37.

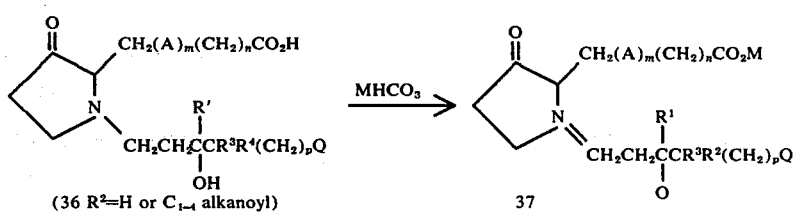

Addition of 1 equivalent of the strong acid HX (X=Cl, Br, I) to a solution of 36 ($R^2$=H or $C_{1-4}$ alkanoyl) in ether affords the sparingly soluble salts 38, or these salts can be prepared

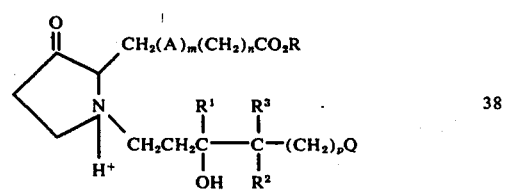

by addition of 2 equivalents of HX to an aqueous solution of 37. Amine salts 39 can be prepared by addition of 1 equivalent of amine $R_3N$ to the acids 36 $R^2$=H or $C_{1-4}$ alkanoyl:

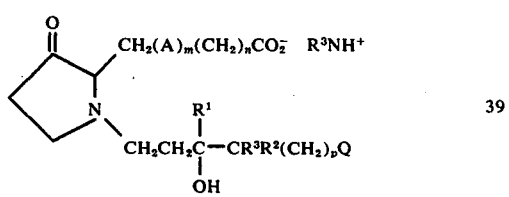

Table I

| Column A | Column B |
|---|---|
| (omega-halo esters) | (2-amino dicarboxylic acid ester hydrochloride) |
| a. $I(CH_2)_6CO_2Et$ | a. $CH_3O_2C-CH(CH_2)_6CO_2CH_3$ <br>       $\quad\quad\quad\quad\quad\; \|$ <br> $\quad\quad\quad\quad\quad\; NH_3^+Cl^-$ |
| b. $Br(CH_2)_5CO_2CH_3$ | b. $CH_3O_2C-CH(CH_2)_5CO_2CH_3$ <br> $\quad\quad\quad\quad\quad\; \|$ <br> $\quad\quad\quad\quad\quad\; NH_3^+Cl^-$ |
| c. $Br(CH_2)_3CO_2Et$ | c. $EtO_2C-CH(CH_2)_3CO_2Et$ <br> $\quad\quad\quad\quad\quad\; \|$ <br> $\quad\quad\quad\quad\quad\; NH_3^+Cl^-$ |
| d. $BrCH_2-\langle○\rangle-CH_2CH_2CO_2tBu$ | d. $CH_3O_2C-CH-CH_2-\langle○\rangle-CH_2CH_2CO_2CH_3$ <br> $\quad\quad\quad\quad\; \|$ <br> $\quad\quad\quad\quad\; NH_3^+Cl^-$ |
| e. $BrCH_2-\langle○\rangle-(CH_2)_4CO_2Et$ | e. $CH_3O_2C-CH-CH_2-\langle○\rangle-(CH_2)_4CO_2CH_3$ <br> $\quad\quad\quad\quad\; \|$ <br> $\quad\quad\quad\quad\; NH_3^+Cl^-$ |
| f. $BrCH_2-\langle○\rangle^{CO_2CH_3}$ | f. $CH_3O_2C-CH-CH_2-\langle○\rangle^{CO_2CH_3}$ <br> $\quad\quad\quad\quad\; \|$ <br> $\quad\quad\quad\quad\; NH_3^+Cl^-$ |
| g. $ICH_2-\langle○\rangle^{CO_2CH_3}$ | g. $CH_3O_2C-CH-CH_2-\langle○\rangle^{CO_2CH_3}$ <br> $\quad\quad\quad\quad\; \|$ <br> $\quad\quad\quad\quad\; NH_3^+Cl^-$ |
| h. $BrCH_2C\equiv C(CH_2)_3CO_2Et$ | h. $CH_3O_2C-CH-CH_2C\equiv C(CH_2)_3CO_2CH_3$ <br> $\quad\quad\quad\quad\; \|$ <br> $\quad\quad\quad\quad\; NH_3^+Cl^-$ |
| i. $BrCH_2C\equiv C(CH_2)_2CO_2Et$ | i. $CH_3O_2C-CHCH_2C\equiv C(CH_2)_2CO_2CH_3$ <br> $\quad\quad\quad\quad\; \|$ <br> $\quad\quad\quad\quad\; NH_3^+Cl^-$ |
| j. $ICH_2CH\overset{(c)}{=}CH(CH_2)_3CO_2Et$ | j. $CH_3O_2CCH-CH_2CH\overset{(c)}{=}CH(CH_2)_3CO_2CH_3$ <br> $\quad\quad\quad\quad\; \|$ <br> $\quad\quad\quad\quad\; NH_3^+Cl^-$ |
| k. $BrCH_2CH\overset{(c)}{=}CH(CH_2)_2CO_2Et$ | k. $CH_3O_2C-CH-CH_2CH\overset{(c)}{=}CH(CH_2)_2CO_2CH_3$ <br> $\quad\quad\quad\quad\; \|$ <br> $\quad\quad\quad\quad\; NH_3^+Cl^-$ |

| Column C | Column D |
|---|---|
| (4-Biphenylcarbonyl Derivatives) | (3-Pyrrolidone Amides) |
| a. $CH_3O_2C-CH(CH_2)_6CO_2CH_3$ <br> $\quad\quad\quad\quad\; \|$ <br> $\quad\quad\quad\quad\; NHCOBP$ | a. 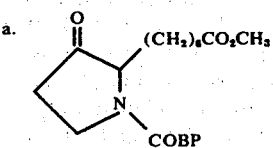 |
| b. $CH_3O_2CCH(CH_2)_5CO_2CH_3$ <br> $\quad\quad\quad\; \|$ <br> $\quad\quad\quad\; NHCOBP$ | b. 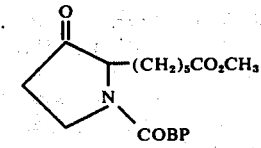 |
| c. $EtO_2C-CH(CH_2)_3CO_2Et$ <br> $\quad\quad\quad\; \|$ <br> $\quad\quad\quad\; NHCOBP$ | c. 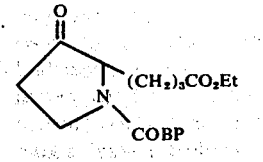 |

Table I-continued
d. 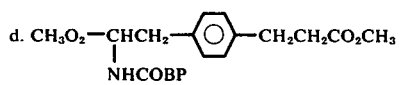
d. 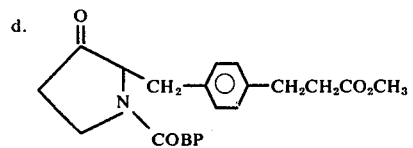
e. 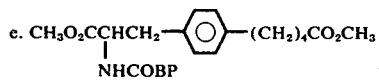
e. 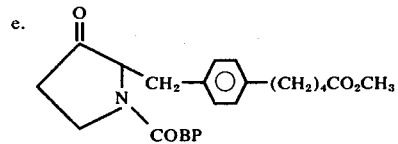
f. 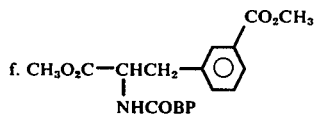
f. 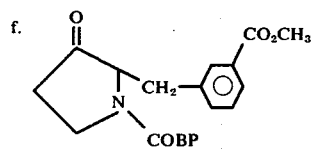
g. 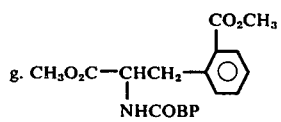
g. 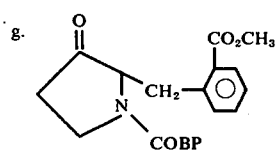
h. 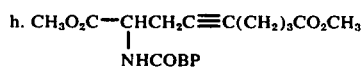
h. 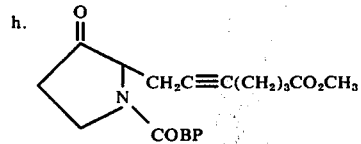
i. 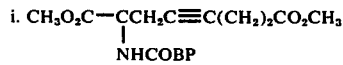
i. 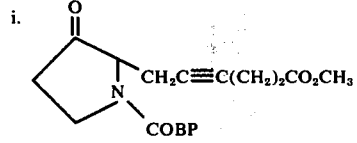
j. 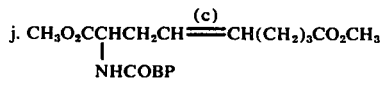
j. 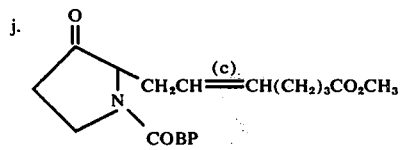
k. 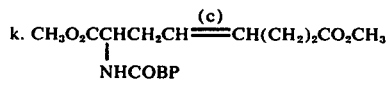
k. 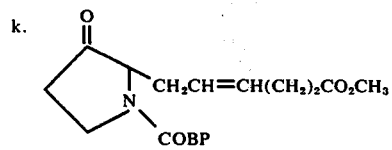
Column E
Column F
(Ketal Ester Amides)
(Ketal Amines)
a. 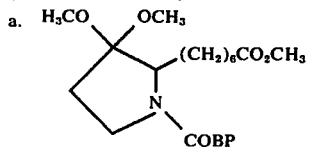
a. 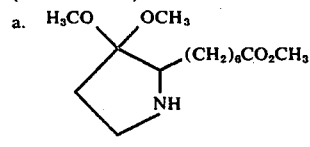
b. 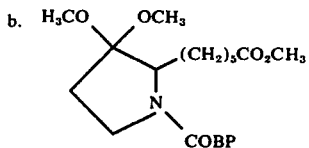
b. 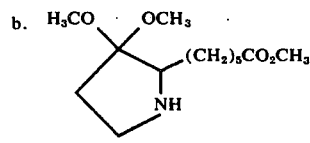

Table I-continued
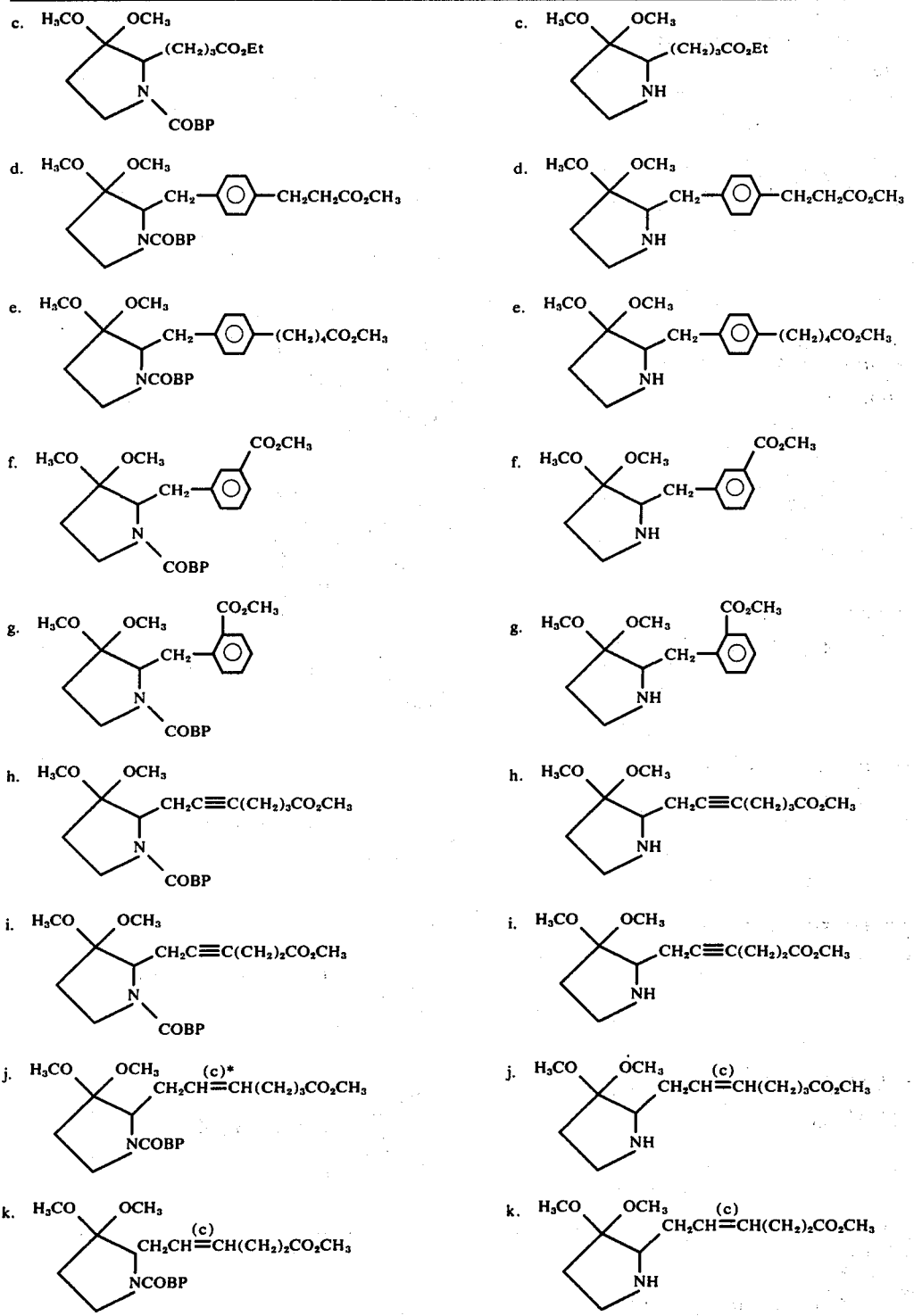
Column G
(Vinyl Ketones)
a. $CH_2=CHCOCF_2C_5H_{11}(n)$
Column H
(Ketal Amino Ketones)
a. 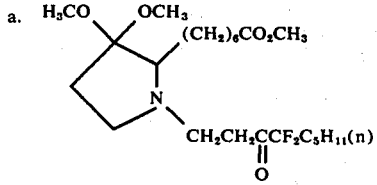

Table I-continued
b. CH₂=CHCOCHFCH₂CF₂CH₃ 
b. 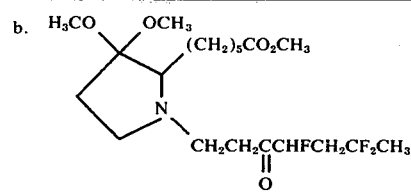
c. CH₂=CHCOCHFC₆H₁₃(n) 
c. 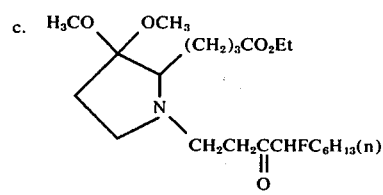
d. CH₂=CHCOC₈H₁₇(n) 
d. 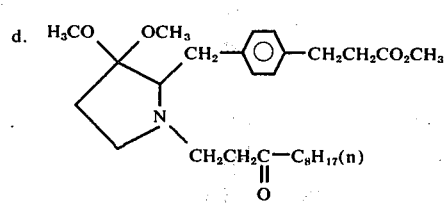
e. CH₂=CHCOC(CH₃)₂(CH₂)₃CF₃ 
e. 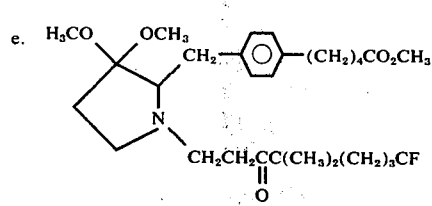
f. CH₂=CHCOCH₃ 
f. 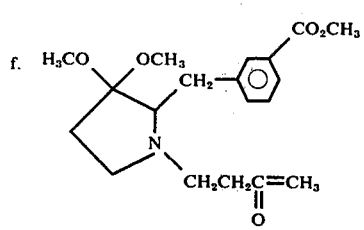
g. CH₂=CHCOCF₂CH₂CH₂— 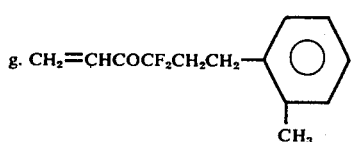
g. 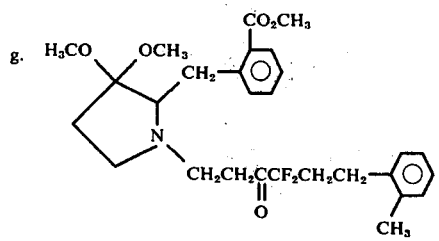
h. CH₂=CHCOC₇H₁₅(n) 
h. 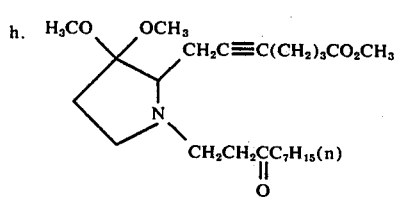
i. CH₂=CHC—(CH₂)₃—⟨⟩—CH(CH₃)₂ 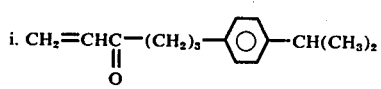
i. 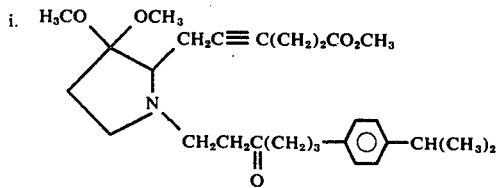

Table I-continued
j. CH₂=CHCOC₅H₁₁(n)
j. 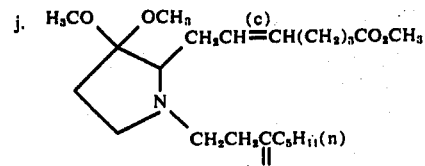
k. CH₂=CHCOCH(CH₃)(CH₂)₂CF₂CH₃
k. 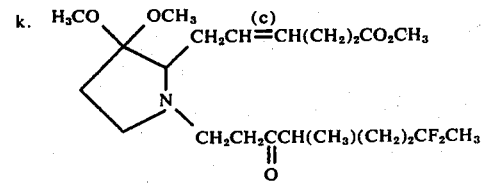
| Column I | Column J |
|---|---|
| (Ketal Amino Alcohols) | (3-pyrrolidones) |
| a. 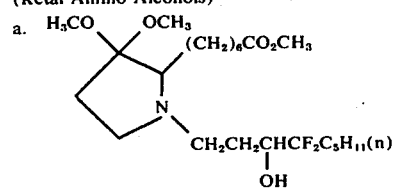 | a. 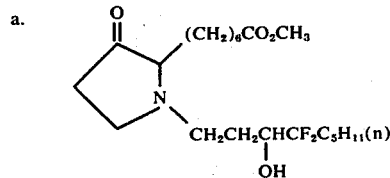 |
| b. 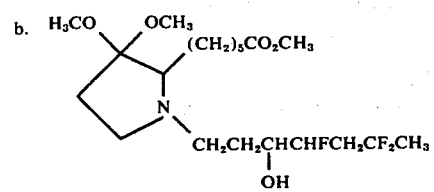 | b. 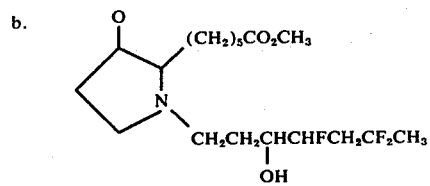 |
| c. 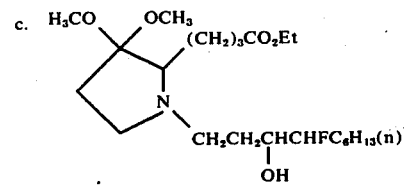 | c. 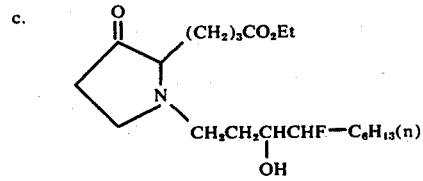 |
| d. 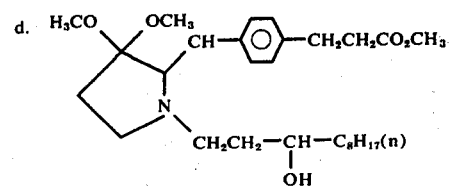 | d. 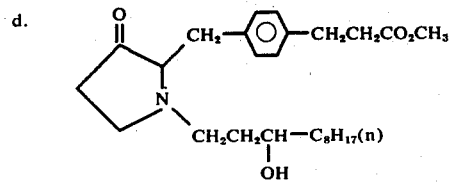 |
| e. 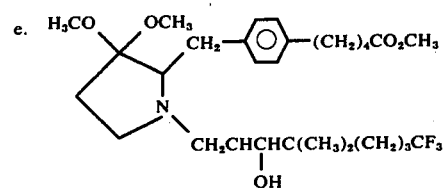 | e. 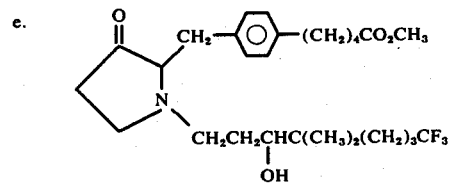 |
| f. 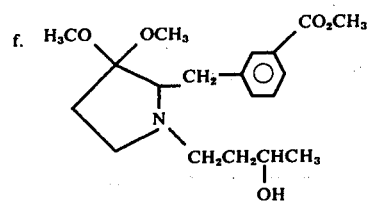 | f. 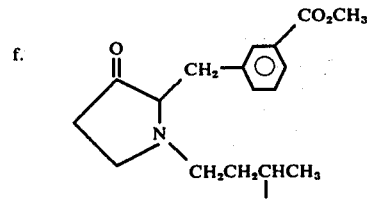 |

Table I-continued
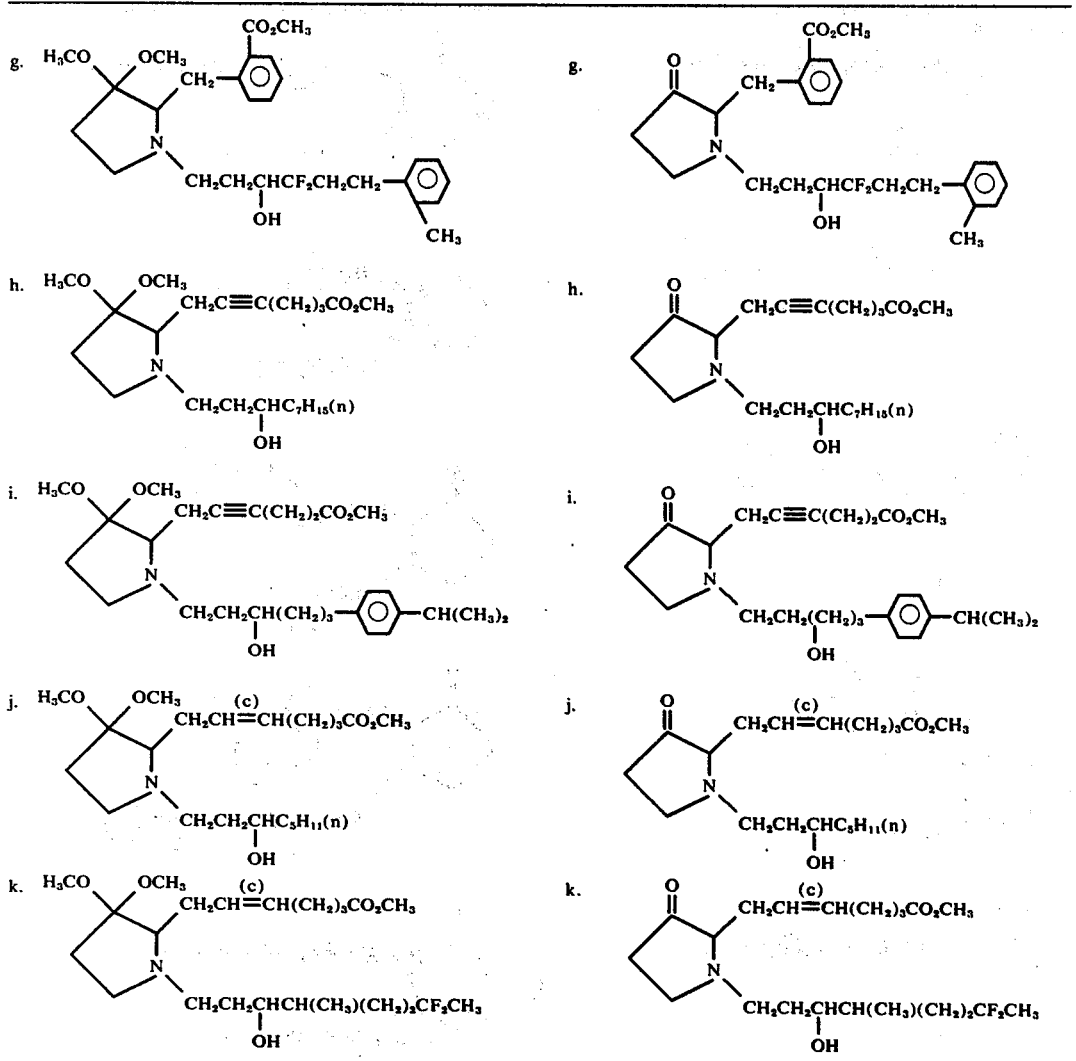
Column K
(Ketal Ester Amides)
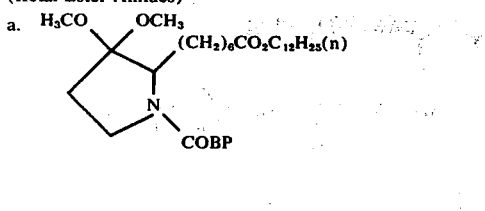
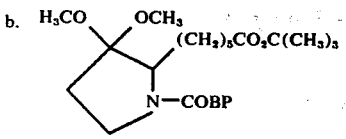
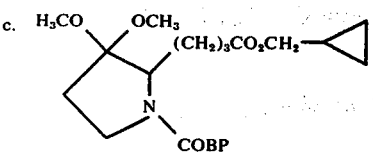
Column L
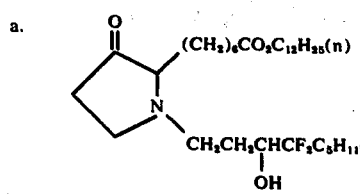
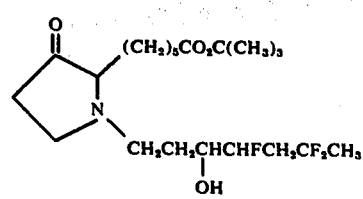
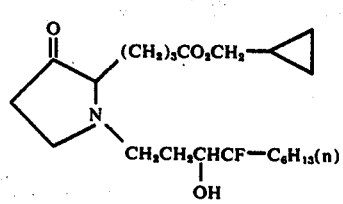

Table I-continued
d. 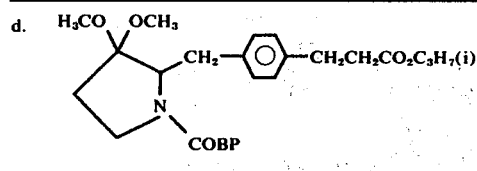  d. 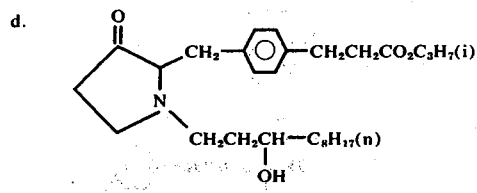
e. 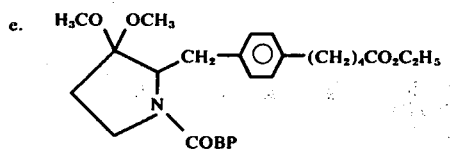  e. 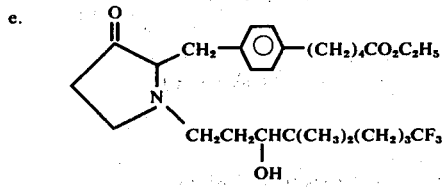
f. 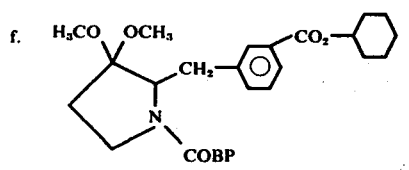  f. 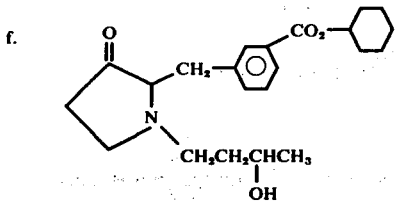
g. 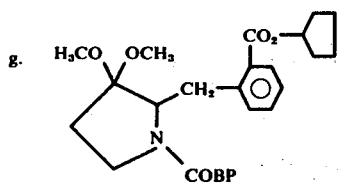  g. 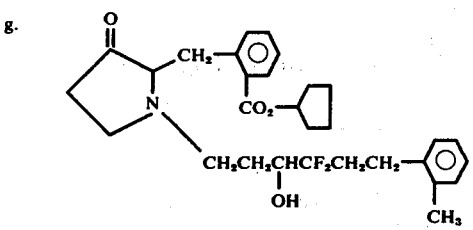
h. 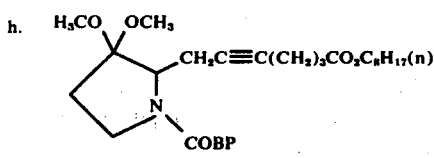  h. 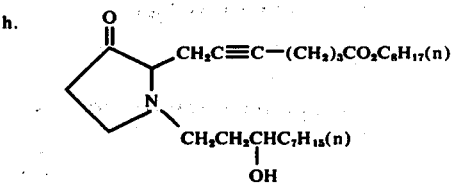
i. 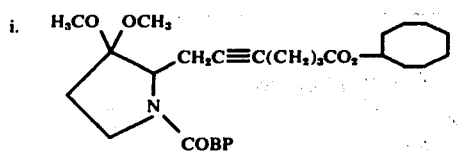  i. 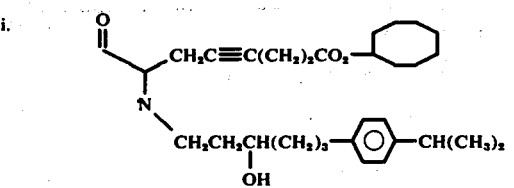
j. 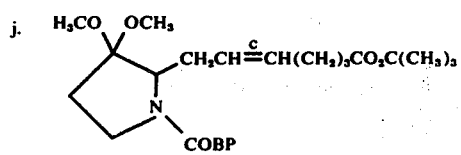  j. 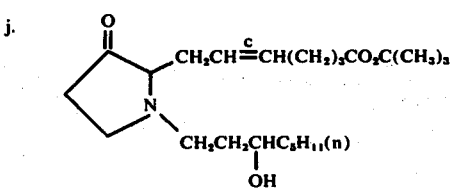
k. 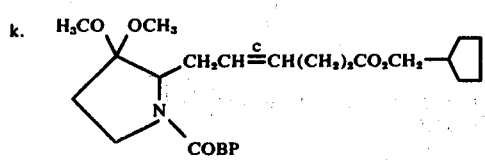  k. 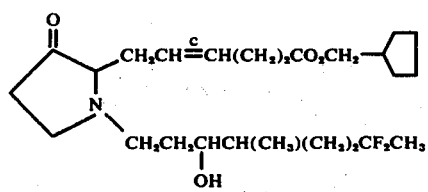
Column M                 Column N Table I-continued
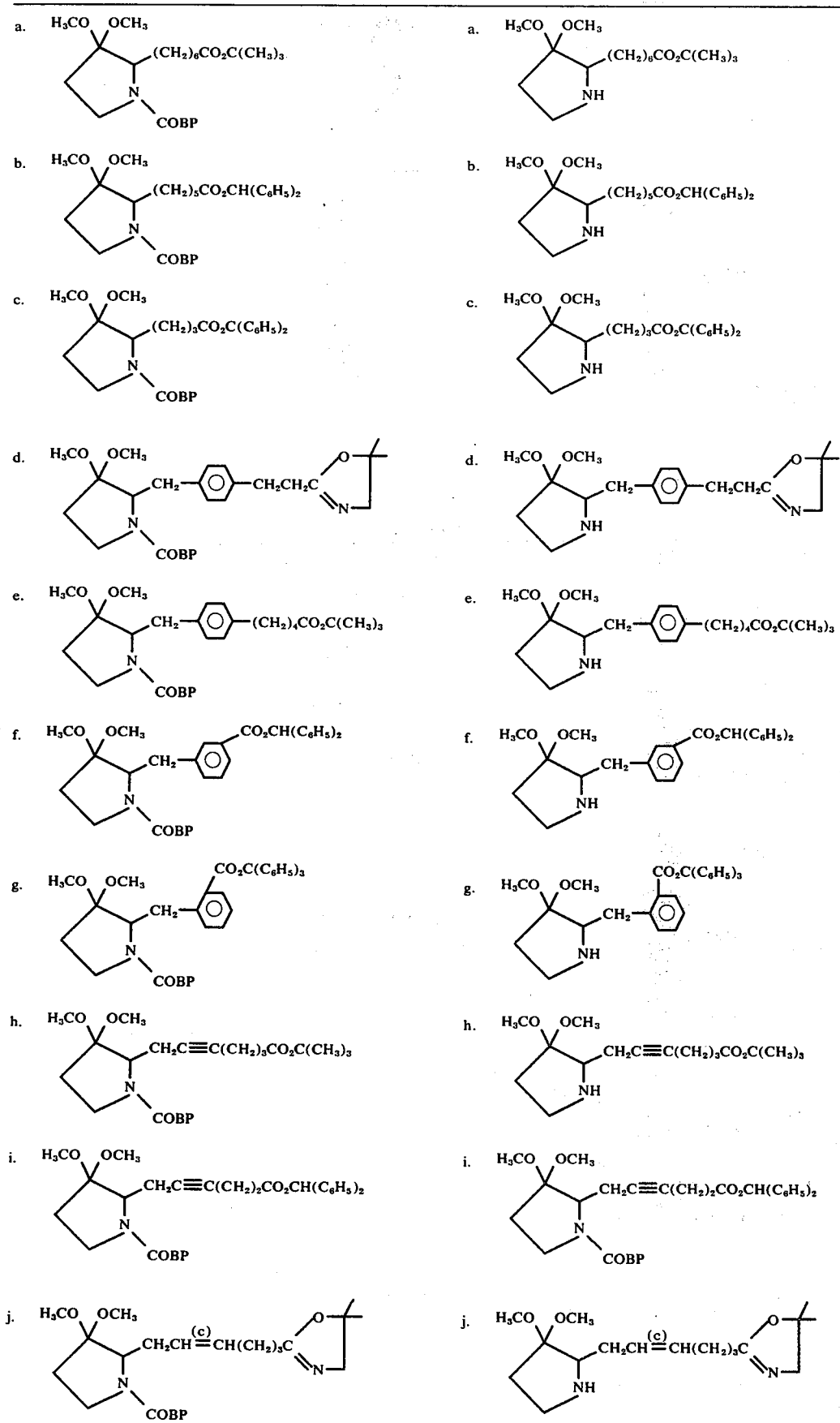

Table I-continued
k. 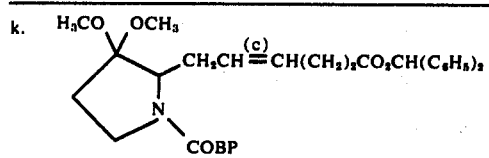   k. 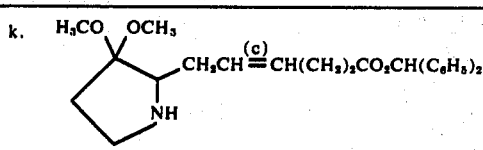
Column O
(vinyl ketones)
a. $CH_2=CHCOC_7H_{15}(n)$
b. $CH_2=CHCO(CH_2)_4CF_3$
c. 
d. 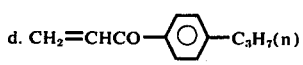
e. $CH_2=CHCO(CH_2)_3CF_2CH_3$
f. $CH_2=CHCOCH_2CH_3$
g. $CH_2=CHCO(CH_2)_9CH_3$
h. $CH_2=CHCOC_5H_{11}(n)$
i. $CH_2=CHCOC_6H_{13}(n)$
j. $CH_2=CHCO(CH_2)_4CF_3$
k. $CH_2=COC_2H_5$
| Column P | Column Q |
|---|---|
| (ketal amino ketones) | (organo metallic reagents) |
| a. 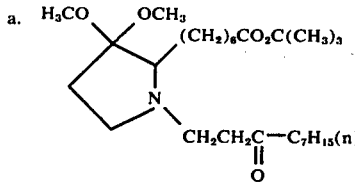 | a. $CH_3MgI$ |
| b. 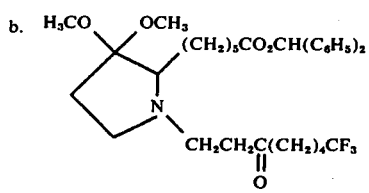 | b. $C_2H_5MgBr$ |
| c. 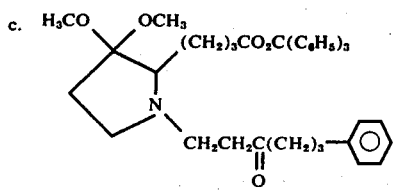 | c. $CH_2=CHMgBr$ |
| d. 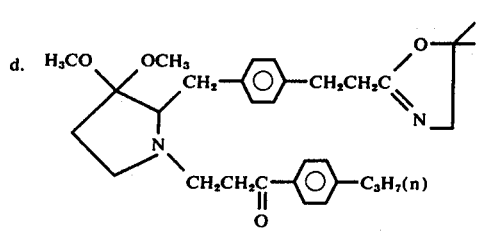 | d. $CH_2=CHLi$ |
| e. 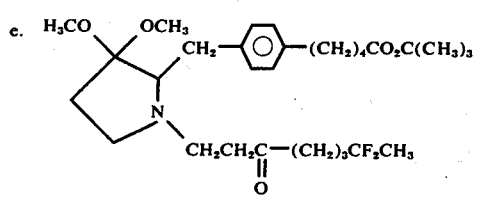 | e. $HC\equiv CNa$ |

Table I-continued
f. 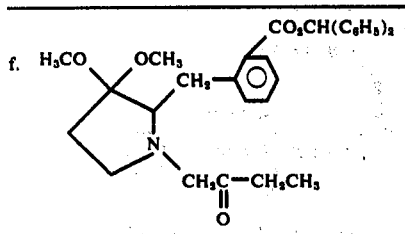  f. $CH_2=CHMgBr$
g. 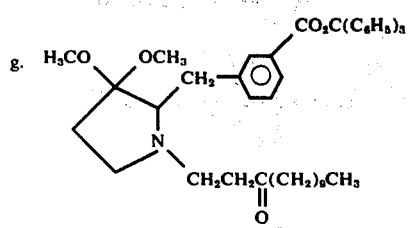  g. $HC\equiv CNa$
h. 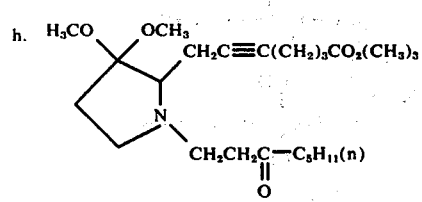  h. $CH_3MgBr$
i. 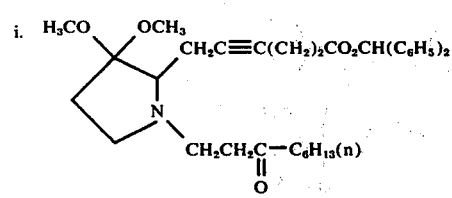  i. $HC\equiv CNa$
j. 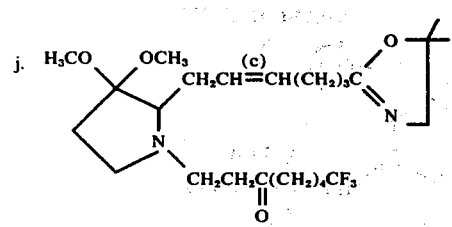  j. $CH_3MgBr$
k. 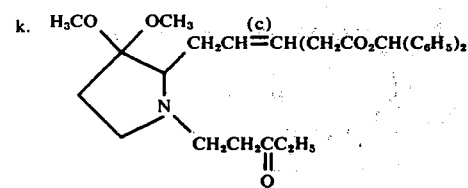  k. $C_2H_5MgBr$
Column R  
(tertiary alcohols)
a. 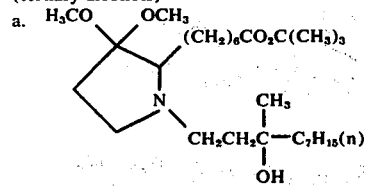
Column S  
(tertiary alcohols, esters and acid)
a. 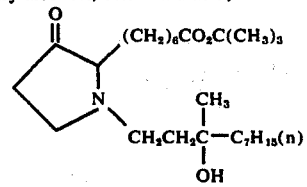
b. 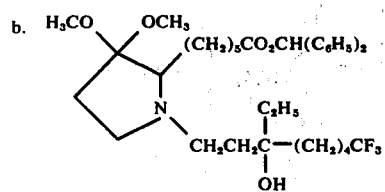

Table I-continued
c. 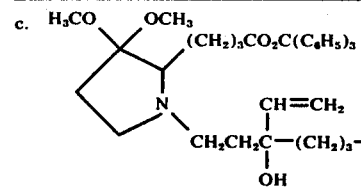
c. 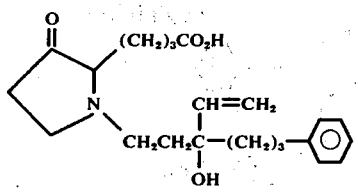
d. 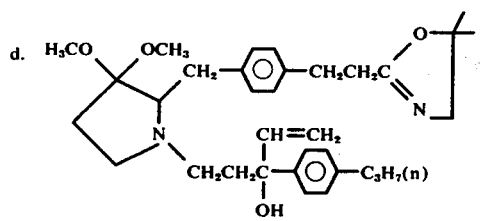
d. 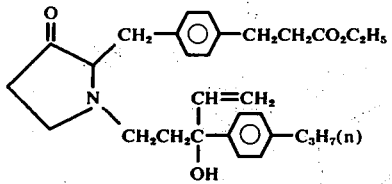
e. 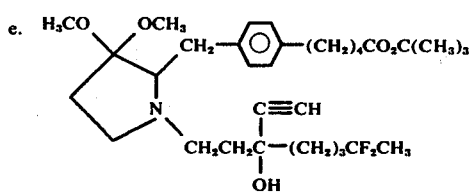
e. 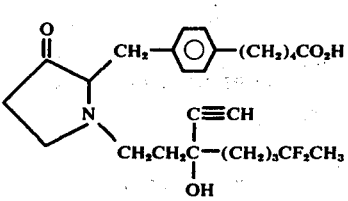
f. 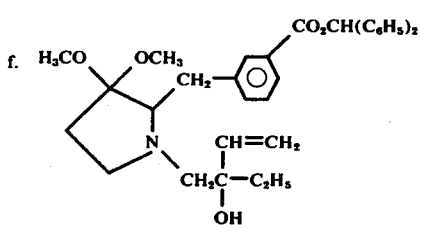
f. 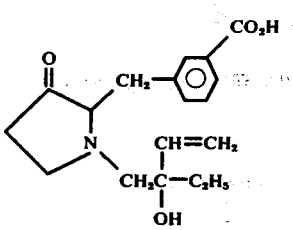
g. 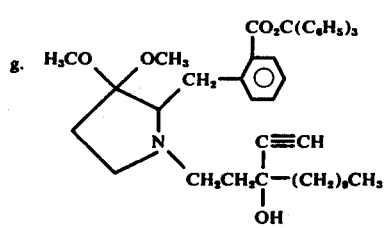
g. 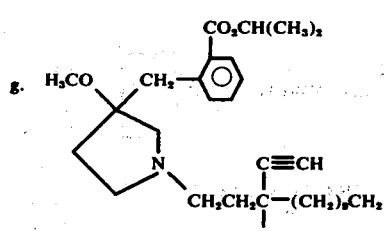
h. 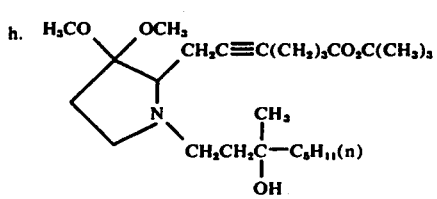
h. 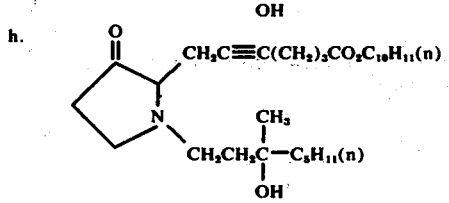
i. 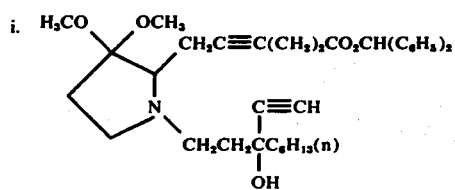
i. 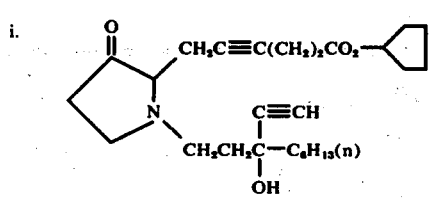
j. 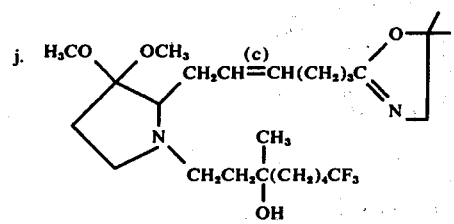
j. 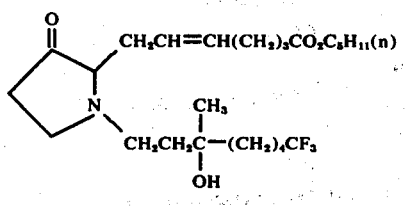

Table I-continued

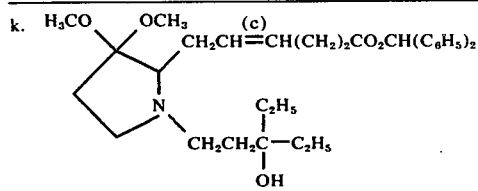

*(c) = cis

2,4-Pyrrolidindiones

A. Amino Ketones

The α-amino diester hydrochlorides 4, exemplified by those listed in Col. B (Table I), are also used as precursors to the 2,4-pyrrolidinones. These hydrochlorides 4 are first converted to the free amines by treatment with 1 molar equivalent of base. For example, the hydrochlorides 4 can be dissolved in water, treated with a slight excess of an alkali metal hydroxide, and extracted into ether as the free amine. Or, as in Example N, a solution of the hydrochloride 4 in an alcohol can be treated with one equivalent of sodium alcoholate to generate the free amine in alcoholic solution which is then used directly in the following step. The free amine obtained either way is treated with a vinyl ketone in glyme, tetrahydrofuran, ether, or an alcohol as the solvent, affording the amino ketone 40. Amine ketone 40 can be purified as the hydrochloride salt 20 if desired.

Col. A (Table II) are converted by reaction with the corresponding vinyl ketones of Col. B (Table II) to the corresponding amino ketones (40) of Col. D (Table II).

Often better yields of the amino ketones 40 can be obtained by using the reactions of acetylenic ketones $HC\equiv CCOCR^2R^3CO(CH_2)_pQ$ with the amines derived from the salt 4. This affords the unsaturated amino ketones 41 which in turn are hydrogenated in the presence of at least one equivalent of acid, preferably hydrochloric acid, and in the presence of a hydrogenation catalyst, preferably rhodium on carbon, to give amino ketone salt 20. Example N typifies this procedure.

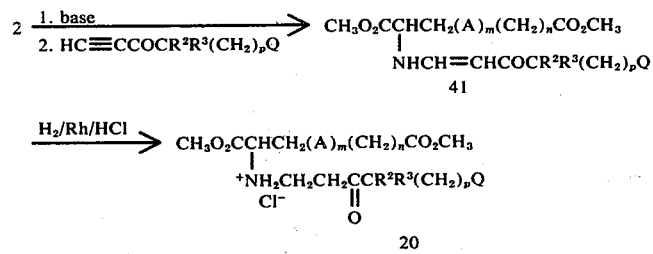

In similar manner the acetylenic ketones of Col. C (Table II) react with the corresponding amino esters of Col. A (Table II) to afford the corresponding amino ketone hydrochlorides of Col. D (Table II).

The acetylenic ketones $HC\equiv CCOCR^2R^3(CH_2)_pQ$ can be prepared by several alternate routes analogous to those described for preparation of the corresponding vinyl ketones. For example (Method 1) propiolalde-

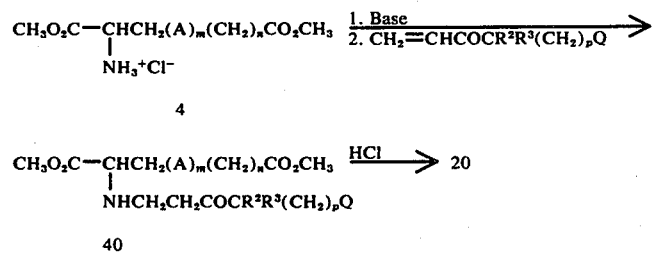

Hydrochloride salts 20 tend to be more stable than the parent amino ketones 40. Thus, the hydrochlorides 4 of hyde is treated with the

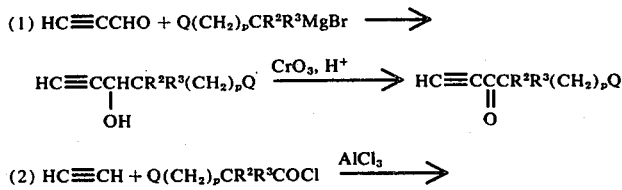

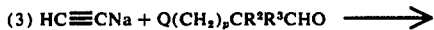

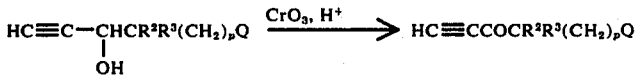

Grignard reagent derived from $Q(CH_2)_pCR^2R^3X$ where X is halogen, preferably chlorine, affording an acetylenic carbinol which in turn is oxidized with chromic acid to the acetylenic ketone. Care must be taken that the aldehyde be added very slowly to cold Grignard reagent lest the aldehyde undergo extremely vigorous decomposition or polymerization. Method (2) involves addition of excess acetylene to an acyl chloride in the presence of a Friedel-Crafts catalyst such as aluminum chloride. Finally, in Method (3) sodium acetylide is allowed to react with a suitable aldehyde to afford an acetylenic carbinol, which in turn is oxidized by chromic acid to give the acetylenic ketone. Of these three methods (2) and (3) are usually the most satisfactory. Thus 6,6,6 trifluorohexanoic acid chloride (prepared via adipic acid monomethyl ester and $SF_4$) reacts smoothly as its complex with aluminum chloride in nitromethane with excess acetylene (Method 2) to give a good yield of 8,8,8-trifluoro-1-octyn-3-one. Likewise, the acid chloride of 4 (p-chlorophenyl)butyric acid gives 6-(p-chlorophenyl)-1-hexyn-3-one. Hexaldehyde readily reacts with acetylene in glyme in the presence of powdered KOH to give an acetylenic carbinol which in turn is oxidized by a solution of $CrO_3$ in water and sulfuric acid to 1-octyn-3-one (Method 3).

B. Amino Alcohols

The amino ketones 20 or their hydrochlorides 40 can be reduced directly to the corresponding amino alcohols by borohydride reagents such as $NaBH_4$ and then the amino alcohol can be isolated as the hydrochlorides 21 as in Example N.

sec-butylborohydride affords the corresponding secondary alcohols of Col. E (Table II). Or reaction of the compounds of Col. D (Table II) with the corresponding organometallic reagents of Col. F (Table II) gives the corresponding amino tertiary alcohols of Col. G (Table II).

C. N-Ethoxycarbonylacetyl Derivatives

As in Example O the amino alcohols (21) of Col. E (Table II) are treated with 1 molar equivalent of ethoxycarbonylacetyl chloride in the presence of at least two molar equivalents of a tertiary amino such as triethylamine to afford the corresponding amines of Col. H (Table II). Likewise the amino tertiary alcohols (42) of Col. G (Table II) on treatment with ethoxycarbonylacetyl chloride afford the corresponding amides of Col. I (Table II).

D. 3-Carboethoxy-2,4-pyrrolidindiones

As in Example P the N-ethoxycarbonylacetyl derivatives (22) of Col. H (Table II) are treated with at least one equivalent of a sodium alcoholate, preferably sodium methoxide in the case of the methyl esters and sodium ethoxide in the case of the ethyl esters, to give the corresponding 3-carboethoxy-2,4-pyrrolidindiones 23 which, without purification, are hydrolyzed and decarboxylated with slightly more than one equivalent of 0.1N HCl to afford the corresponding 2,4-pyrrolidindiones 24 of Col. J. Hydrolysis and decarboxylation of these 3-carboethoxy-2,4-pyrrolidindiones can also be accomplished smoothly by refluxing in moist acetonitrile for several hours. (The reaction can be followed by testing an aliquot with methanolic ferric

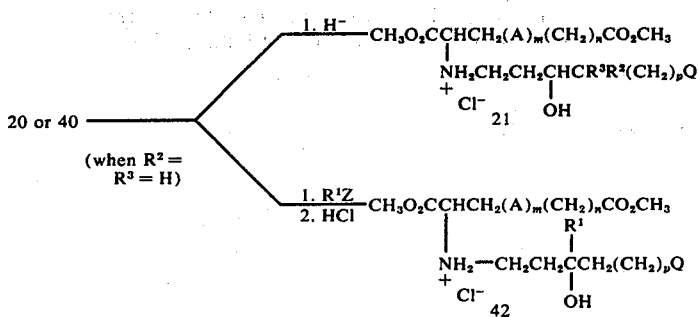

The amino ketones 20 or their hydrochlorides 40 when $R^2=R^3=H$ can be allowed to react with one mole (in the case of the amino ketones 20) or with two moles (in the case of their hydrochlorides 40) of the organometallic reagent $R^1Z$ to give the tertiary alcohols. These tertiary alcohols generally have to be purified by column chromatography and then they can be isolated as their hydrochloride salts 42 simply by passing gaseous HCl into a solution of the amino alcohol in ether and collecting the sparingly soluble hydrochloride salt by filtration.

Thus, reduction of amino ketones 20 or hydrochlorides 40 of Col. D (Table II) with a borohydride reducing agent such as $NaBH_4$, $Zn(BH_4)_2$, or potassium trichloride which gives a purple or red color in the presence of unchanged β-keto ester.)

Likewise the N-ethoxycarbonylacetyl derivatives of Col. 1 (Table II) are converted under the same conditions to the 2,4-pyrrolidindiones of Col. K (Table II).

E. Other Esters, Salts, and Acids

Under alkaline conditions or on heating with mineral acid the 2,4-pyrrolidindiones 24 tend to undergo dehydrodimerization. Hence conversion of these esters into the corresponding salts or carboxylic acids is best carried out on their precursor 3-carboethoxy derivatives 23 under mild conditions. The following flow chart summarizes the preferred routes to other esters and the salts and acids derived from the 2,4-pyrrolidindiones 23.

of Col. J are converted to the new esters typified by the corresponding esters b, f, and j of Col. L and the esters

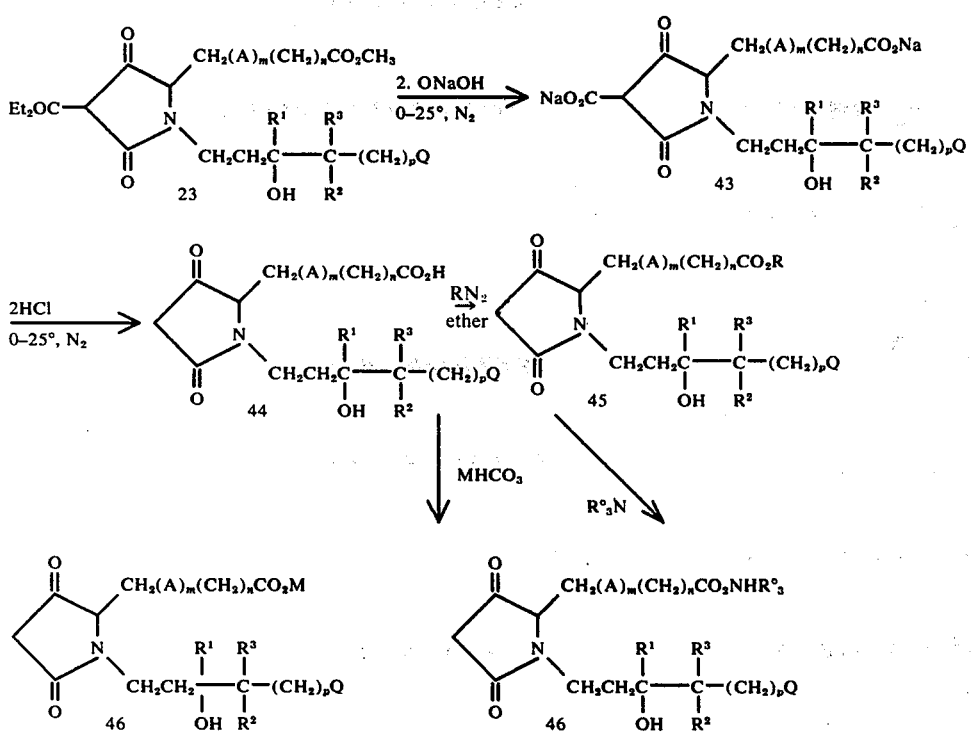

Saponification of the diesters 23 can be carried out using exactly 2 equivalents of 0.1N NaOH in methanol under nitrogen at 0°–25°, preferably with cooling at about 5°. Generally 24 hr at 5° suffices for this saponification. Acidification of the disodium salt 43 thus obtained using exactly 2 equivalents of 0.1N HCl under a nitrogen atmosphere at 0°–25° gives the monocarboxylic acid 44 which can be extracted into ether and purified by chromatography on silica gel. Thus, the carboxylic acids corresponding to all the esters of Cols. J and K (Table II) can be prepared. These acids are exemplified by compounds a, , and j of Col. L, prepared from the 3-carboethoxy-2,4-pyrrolidindione precursors to the corresponding esters of Col. J, and by compounds c, h, and k of Col. M, prepared from the 3-carboethoxy-2,4-pyrrolidindione precursors to the corresponding esters of Col. K (Table II).

The carboxylic acids 44 are useful as precursors to a variety of esters but esterification must be carried out under neutral conditions, e.g., with diazalkanes $RN_2$ or with alcohols ROH in the presence of reagents such as N,N¹-dicyclohexylcarbodiimide or ethoxyacetylene. Thus, the carboxylic acids corresponding to the esters of Col. K are converted to the new esters typified by the corresponding esters d and i of Col. M (Table II).

The carboxylic acids 44 are also useful as precursors to the salts 47. Reaction of a methanol-water solution of the acids corresponding to the esters of Cols. K and L (Table II) with one equivalent of $MHCO_3$ where M is an alkali metal such as Na, K or Li gives the corresponding metal salt 46 isolated simply by evaporation of the solvent. Thus the acid corresponding to esters c, g, and i of Col. J afford the corresponding sodium salts of Col. L on treatment with $NaHCO_3$ and the acids corresponding to esters a, e, and f of Col. K afford the corresponding potassium salts of Col. M on treatment with $KHCO_3$.

Treatment of ether solutions of the acids corresponding to the esters of Cols. K and L with equivalent amounts of the tertiary amines, e.g., trimethylamine, triethylamine gives the corresponding amine salts. Thus, treatment of the acids corresponding to the esters d and h of Col. J with trimethylamine b, g, and j gives the corresponding amine salts of Col. L (Table II) and treatment of the acids corresponding to the esters of Col. K with triethylamine gives the corresponding amine salts of Col. M (Table II).

TABLE II

| | Column A (α-amino diester hydrochlorides) | | Column B (vinyl ketones) |
|---|---|---|---|
| a. | $CH_3O_2CCH(CH_2)_6CO_2CH_3$<br>\|<br>$NH_3{}^+CO^-$ | a. | $CH_2{=}CHCOC_7H_{15}(n)$ |
| b. | $CH_3O_2CCH(CH_2)_6CO_2CH_3$<br>\|<br>$NH_3{}^+Cl^-$ | b. | — |

TABLE II-continued

| | | | |
|---|---|---|---|
| c. | EtO$_2$CCH(CH$_2$)$_3$CO$_2$Et<br>\|<br>NH$_3$$^+$Cl$^-$ | c. | CH$_2$=CHCO(CH$_2$)$_3$—⟨O⟩—(CH$_3$)$_2$ |
| d. | CH$_3$O$_2$CCHCH$_2$—⟨O⟩—(CH$_2$)$_4$CO$_2$CH$_3$<br>\|<br>NH$_3$$^+$Cl$^-$ | d. | CH$_2$=CHCOCH(CH$_3$)$_2$(CH$_2$)$_2$CF$_2$CH$_3$ |
| e. | CH$_3$O$_2$CCHCH$_2$—⟨O⟩—(CH$_2$)$_4$CO$_2$CH$_3$<br>\|<br>NH$_3$$^+$Cl$^-$ | e. | — |
| f. | CH$_3$O$_2$CCHCH$_2$—⟨O⟩(CO$_2$CH$_3$)<br>\|<br>NH$_3$$^+$Cl$^-$ | f. | CH$_2$=CHCOCHFC$_6$H$_{13}$(n) |
| g. | CH$_3$O$_2$C—CH—CH$_2$C≡C(CH$_2$)$_3$CO$_2$CH$_3$<br>\|<br>NH$_3$$^+$Cl$^-$ | g. | CH$_2$=CHCOC(CH$_3$)$_2$(CH$_2$)$_3$CF$_3$ |
| h. | CH$_3$O$_2$C—CH—CH$_2$C=C(CH$_2$)$_3$CO$_2$CH$_3$<br>\|<br>NH$_3$$^+$Cl$^-$ | h. | — |
| i. | CH$_3$O$_2$CCHCH$_2$CH$\overset{(c)}{=}$CH(CH$_2$)$_3$CO$_2$Et<br>\|<br>NH$_3$$^+$Cl$^-$ | i. | CH$_2$=CHCO(CH$_2$)$_4$CF$_3$ |
| j. | CH$_3$O$_2$CCHCH$_2$CH$\overset{(c)}{=}$CH(CH$_2$)$_3$CO$_2$Et<br>\|<br>NH$_3$$^+$Cl$^-$ | j. | — |
| k. | H$_3$CO$_2$CCHCH$_2$CH=CH(CH$_2$)$_4$CO$_2$CH$_3$<br>\|<br>NH$_3$$^+$Cl$^-$ | k. | CH$_2$=CHCOCF$_2$CH$_2$CH$_2$—⟨O⟩—CH$_3$ |

| | Column C<br>(acetylenic ketones) | | Column D<br>(amino ketone hydrochlorides) |
|---|---|---|---|
| a. | — | a. | CH$_3$O$_2$CCH(CH$_2$)$_6$CO$_2$CH$_3$<br>\|<br>NH$_2$CH$_2$CH$_2$C—C$_7$H$_{15}$(n)<br>$+$  ‖<br>Cl$^-$  O |
| b. | HC≡C—CO(CH$_2$)$_4$CF$_3$ | b. | CH$_3$O$_2$C—CH(CH$_2$)$_6$CO$_2$CH$_3$<br>\|<br>$^+$NH$_3$CH$_2$CH$_2$C(CH$_3$)$_2$CF$_4$<br>Cl$^-$  ‖  O |
| c. | — | c. | EtO$_2$CCH(CH$_2$)$_3$CO$_2$Et<br>\|<br>$^+$NHCH$_2$CH$_2$C(CH$_2$)$_3$—⟨O⟩—CH(CH$_3$)$_2$<br>Cl$^-$  ‖  O |
| d. | — | d. | CH$_3$O$_2$C—CH—CH$_2$—⟨O⟩—(CH$_2$)$_4$CO$_2$CH$_3$<br>\|$^+$<br>NH$_2$CH$_2$CH$_2$CC(CH$_3$)$_2$(CH$_2$)$_2$CF$_2$CH$_3$<br>Cl$^-$  ‖  O |
| e. | HC≡CCO(CH$_2$)$_3$—⟨O⟩—Cl | e. | CH$_3$O$_2$CHCH$_2$—⟨O⟩—(CH$_2$)$_4$CO$_2$CH$_3$<br>\|<br>$^+$NH$_2$CH$_2$CH$_2$C(CH$_2$)$_3$—⟨O⟩—Cl<br>Cl$^-$  ‖  O |

TABLE II-continued

| | | | |
|---|---|---|---|
| f. | — | f. | CH₃O₂C—CH—CH₂—C₆H₄(CO₂CH₃)<br>　　　　｜<br>　　NH₂CH₂CH₂CCHFC₆H₁₃(n)<br>　　Cl⁻　　‖<br>　　　　　O |
| g. | — | g. | CH₃O₂C—CHCH₂C≡C(CH₂)₃CO₂CH₃<br>　　　　｜　+<br>　　NH₂CH₂CH₂C—C(CH₃)₂(CH₂)₃CF₃<br>　　Cl⁻　　‖<br>　　　　　O |
| h. | HC≡C—CO(CH₂)₂—C₆H₄—Br | h. | CH₃O₂CCHCH₂C≡C(CH₂)₃CO₂CH₃<br>　　　｜<br>　　⁺NH₂CH₂CH₂C(CH₂)₂—C₆H₄—Br<br>　　Cl⁻　　‖<br>　　　　　O |
| i. | — | i. | CH₃O₂C—CHCH₂CH═(c)CH(CH₂)₃CO₂CH₃<br>　　　｜<br>　　⁺NH₂CH₂CH₂C(CH₂)₄CF₃<br>　　Cl⁻　‖<br>　　　　O |
| j. | HC≡CCOC₅H₁₁(n) | j. | CH₃O₂CHCH₂CH═(c)CH(CH₂)₃CO₂CH₃<br>　　　｜<br>　　⁺NH₂CH₂CH₂CC₅H₁₁(n)<br>　　Cl⁻　‖<br>　　　　O |
| k. | — | k. | CH₃O₂CCHCH₂CH═CH(CH₂)₂CO₂CH₃<br>　　　｜<br>　　⁺NH₂CH₂CH₂CCF₂CH₂CH₂—C₆H₄—CH₃<br>　　Cl⁻　‖<br>　　　　O |

| | Column E<br>(amino alcohols) | | Column F<br>(organometallic reagents) |
|---|---|---|---|
| a. | CH₃O₂CH(CH₂)₆CO₂CH₃<br>　　｜<br>　NHCH₂CH₂CHC₇H₁₅(n)<br>　　　　　｜<br>　　　　　OH | a. | CH₃MgBr |
| b. | CH₃O₂CCH(CH₂)₆CO₂CH₃<br>　　｜<br>　NHCH₂CH₂CH(CH₂)₄CF₃<br>　　　　｜<br>　　　　OH | b. | HC≡CNa |
| c. | EtO₂C—CH(CH₂)₃CO₂Et<br>　　｜<br>　NHCH₂CH₂CH(CH₂)₃—C₆H₄—CH(CH₃)₂<br>　　　　｜<br>　　　　OH | c. | H₂C═CHMgBr |
| d. | CH₃O₂CCHCH₂—C₆H₄—(CH₂)₄CO₂CH₃<br>　　｜<br>　NHCH₂CH₂CHC(CH₃)₂(CH₂)₂CF₂CH₃<br>　　　　｜<br>　　　　OH | d. | — |
| e. | CH₃O₂C—CHCH₂—C₆H₄—(CH₂)₄CO₂CH₃<br>　　｜<br>　NHCH₂CH₂CH(CH₂)₃—C₆H₄—Cl<br>　　　　｜<br>　　　　OH | e. | C₂H₅MgBr |

TABLE II-continued

| | | | |
|---|---|---|---|
| f. | 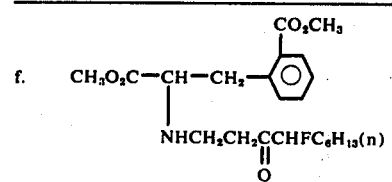 | f. | — |
| g. | 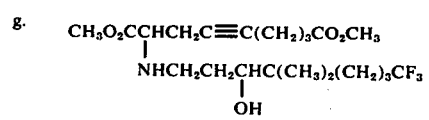 | g. | — |
| h. | 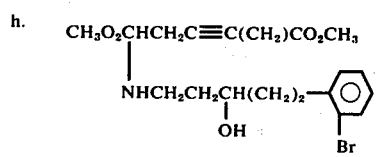 | h. | $CH_3MgBr$ |
| i. | 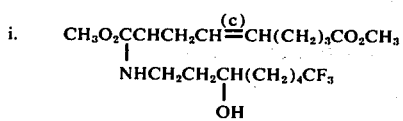 | i. | $CH_2$=$CHMgBr$ |
| j. | 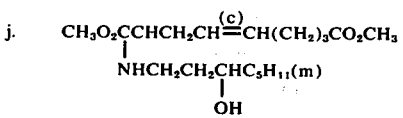 | j. | $CH_3MgBr$ |
| k. | 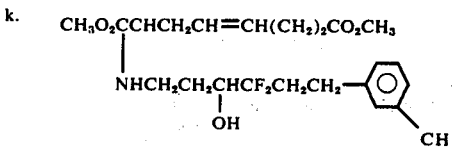 | k. | — |

| | Column G (Amino Tertiary alcohols) | | Column H (N-Ethoxycarbonylacetyl derivatives) |
|---|---|---|---|
| a. | $CH_3O_2CH(CH_2)_6CO_2CH_3$<br>$\quad\vert$<br>$NHCH_2CH_2C\underset{\vert}{\overset{CH_3}{-}}C_7H_{15}(m)$<br>$\qquad\quad OH$ | a. | $CH_3O_2CCH(CH_2)_6CO_2CH_3$<br>$\quad\vert$<br>$EtO_2CCH_2CONCH_2CH_2CH-C_7H_{15}(m)$<br>$\qquad\qquad\qquad\qquad\vert$<br>$\qquad\qquad\qquad\qquad OH$ |
| b. | 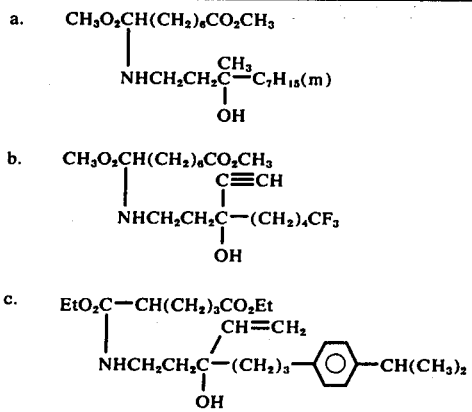 | b. | 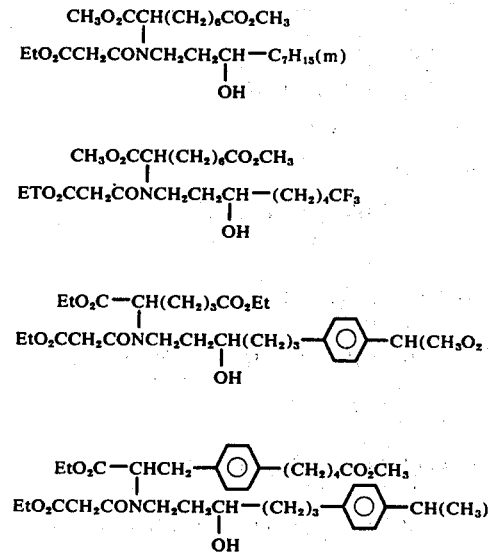 |
| c. | $EtO_2C-CH(CH_2)_3CO_2Et$<br>$\quad\vert\quad\quad\quad CH=CH_2$<br>$NHCH_2CH_2C-(CH_2)_3$-⌬-$CH(CH_3)_2$<br>$\qquad\quad\vert$<br>$\qquad\quad OH$ | c. | $EtO_2C-CH(CH_2)_3CO_2Et$<br>$\quad\vert$<br>$EtO_2CCH_2CONCH_2CH_2CH(CH_2)_3$-⌬-$CH(CH_3O_2)$<br>$\qquad\qquad\qquad\qquad\vert$<br>$\qquad\qquad\qquad\qquad OH$ |
| d. | — | d. | $EtO_2C-CHCH_2$-⌬-$(CH_2)_4CO_2CH_3$<br>$\quad\vert$<br>$EtO_2CCH_2CONCH_2CH_2CH-(CH_2)_3$-⌬-$CH(CH_3)$<br>$\qquad\qquad\qquad\qquad\vert$<br>$\qquad\qquad\qquad\qquad OH$ |
| e. | 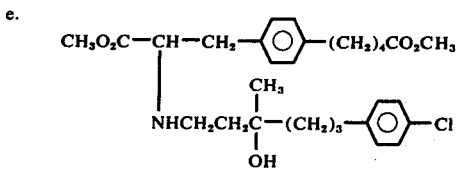 | e. | 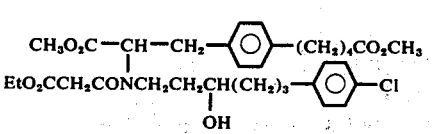 |

TABLE II-continued

| | | | |
|---|---|---|---|
| f. | — | f. | CH₃O₂C—CH—CH₂—[phenyl with CO₂CH₃]<br>EtO₂CCH₂CONCH₂CH₂CHCHFC₆H₁₃(m)<br>                            OH |
| g. | — | g. | CH₃O₂CCHCH₂C≡C(CH₂)₃CO₂CH₃<br>EtO₂CCH₂CONCH₂CH₂CHC(CH₃)₂(CH₂)₃CF₃<br>                            OH |
| h. | CH₃O₂CCHCH₂C≡C(CH₂)₃CO₂CH₃<br>       NHCH₂CH₂C(CH₃)—(CH₂)₂—[phenyl-Br]<br>                  OH | h. | CH₃O₂CCHCH₂C≡C(CH₂)₃CO₂CH₃<br>EtO₂CCH₂CONCH₂CH₂CH(CH₂)₂—[phenyl-Br]<br>                      OH |
| i. | CH₃O₂C—CHCH₂CH=(c)CH(CH₂)₃CO₂CH₃<br>                 CH=CH₂<br>     NHCH₂CH₂C—(CH₂)₄CF₃<br>                OH | i. | CH₃O₂CCHCH₂CH=(c)CH(CH₂)₃CO₂CH₃<br>EtO₂CCH₂CONCH₂CH₂CH(CH₂)₄CF₃<br>                      OH |
| j. | CH₃O₂CCHCH₂CH=(c)CH(CH₂)₃CO₂CH₃<br>                 CH₃<br>    NHCH₂CH₂C—C₅H₁₁(m)<br>               OH | j. | CH₃OCCHCH₂CH=(c)CH(CH₂)₃CO₂CH₃<br>EtO₂CCH₂CONCH₂CH₂CHC₅H₁₁(m)<br>                     OH |
| k. | — | k. | CH₃O₂CCHCH₂CH=(c)CH(CH₂)₂CO₂CH₃<br>EtO₂CCH₂CONCH₂CH₂CHCF₂CH₂—[phenyl-CH₃]<br>                     OH |

| Column I | Column J |
|---|---|
| (N-Ethoxycarbonylacetyl Derivatives) | (2,3-Pyrrolidindiones) |
| a.    CH₃O₂CCH(CH₂)₆CO₂CH₃<br>                         CH₃<br>    EtO₂CCH₂CONCH₂CH₂C—C₇H₁₅(m)<br>                           OH | a.    [2,3-pyrrolidindione with (CH₂)₆CO₂CH₃ and N—CH₂CH₂CHC₇H₁₅(m), OH] |
| b.    CH₃O₂CCH(CH₂)₆CO₂CH₃<br>                      C≡CH<br>    EtO₂CCH₂CONCH₂CH₂C—(CH₂)₄CF₃<br>                         OH | b.    [2,3-pyrrolidindione with (CH₂)₂CO₂CH₃ and N—CH₂CH₂CH(CH₂)₄CF₃, OH] |
| c.    ETO₂CCH(CH₂)₃CO₂Et<br>    EtO₂CCH₂CONCH₂CH₂C—(CH₂)₃—[phenyl]—CH(CH₃)₂<br>                         OH | c.    [2,3-pyrrolidindione with (CH₂)₃CO₂Et and N—CH₂CH₂CH(CH₂)₃—[phenyl]—CH(CH₃)₂, OH] |
| d.    — | d.    [2,3-pyrrolidindione with CH₂—[phenyl]—(CH₂)₄CO₂CH₃ and N—CH₂CH₂CHC(CH₃)₂(CH₃)₂CF₂CH₃, OH] |

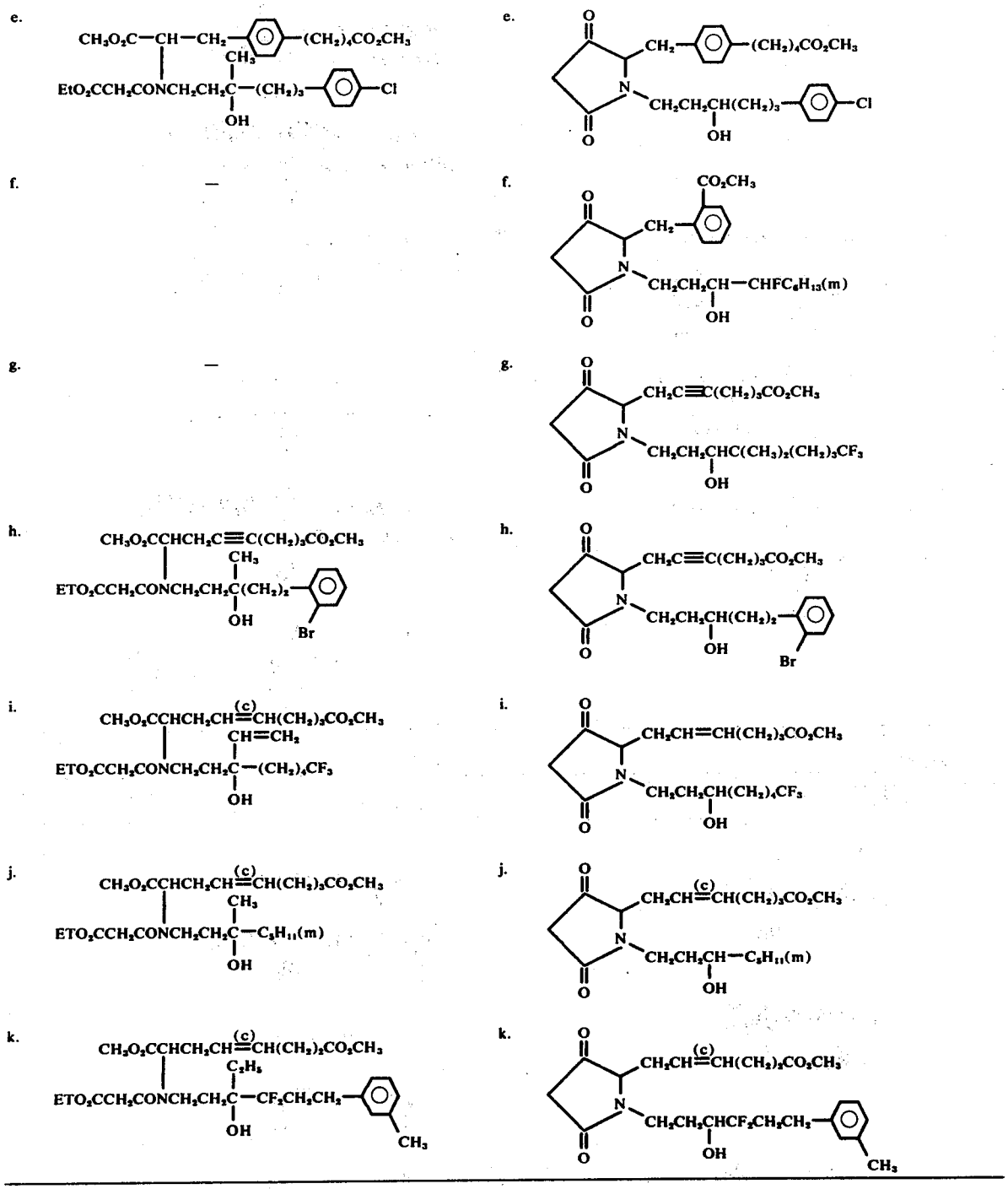

TABLE II-continued
| | | | |
|---|---|---|---|
| b. | 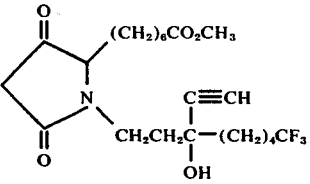 | b. | 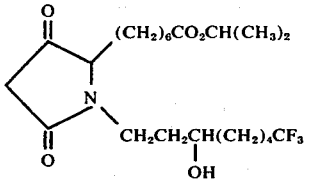 |
| c. | 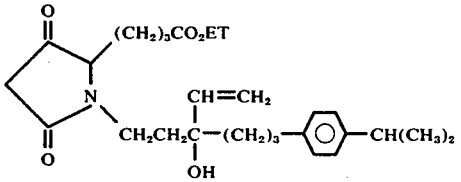 | c. | 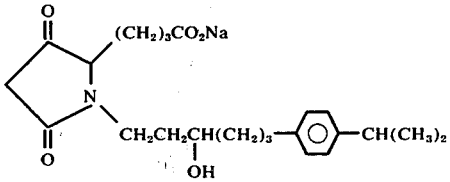 |
| d. | — | d. | 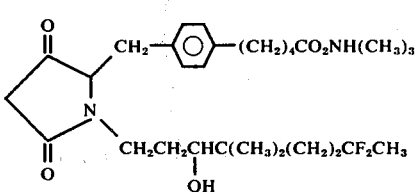 |
| e. | 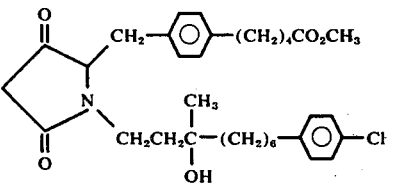 | e. | 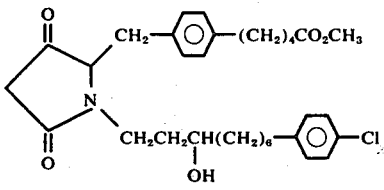 |
| f. | — | f. | 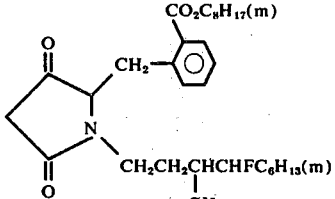 |
| g. | — | g. | 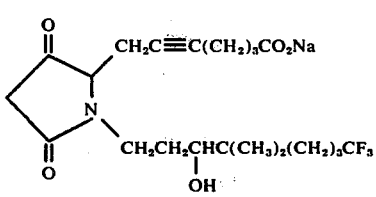 |
Column M
| | |
|---|---|
| d. | 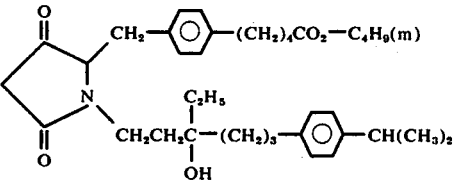 |
| e. | 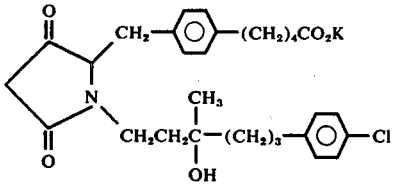 |
| f. | — |

TABLE II-continued
g. —
h. 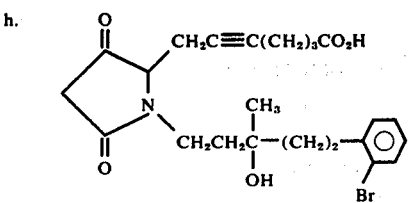
i. 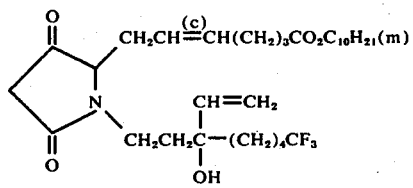
j. 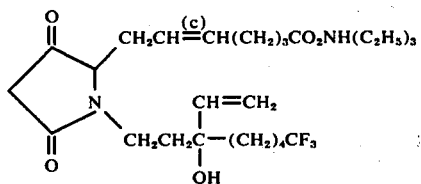
| Column K | Column L |
|---|---|
| h. 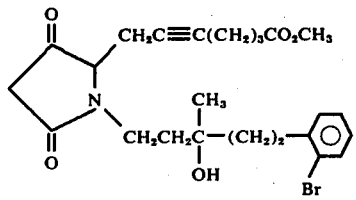 | h. 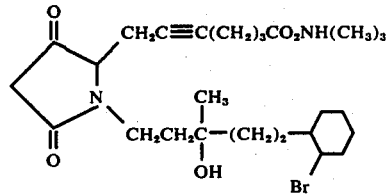 |
| i. 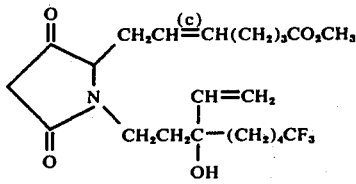 | i. 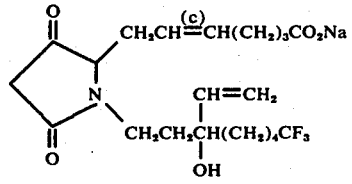 |
| j. 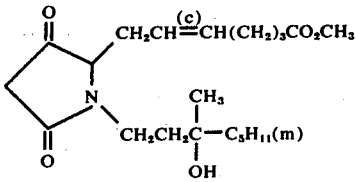 | j. 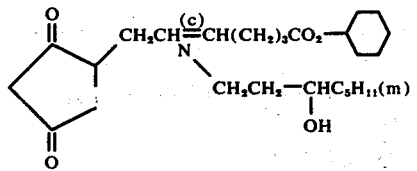 |
| k. — | k. 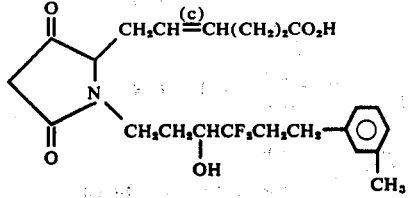 |
Column M

TABLE II-continued

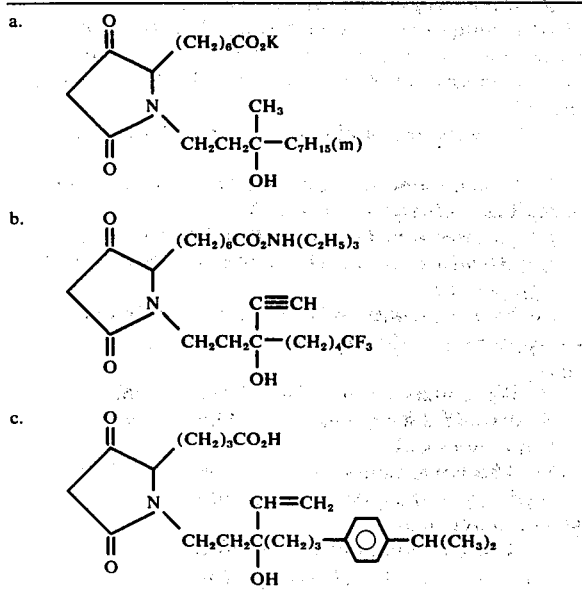

In spite of their relatively high molecular weights, the 3-pyrrolidones and 2,4-pyrrolidindiones of this invention are oils or low melting solids. These compounds are plasticizers for polyvinyl chloride. Thus, 100 mg of one of these 3-pyrrolidones or 2,4-pyrrolidindiones can be added to 2 ml of a tetrahydrofuran solution containing 10% by weight of Geon 128 polyvinyl chloride and the resulting solution can be cast into a film by slow evaporation of the solvent. The resulting film of polyvinyl chloride is more flexible and limp than a control film of Geon 128 polyvinyl chloride containing no added plasticizer.

The 3-pyrrolidones and 2,4-pyrrolidinones also have prostaglandin-like activity; that is, they have biological properties that simulate those of some of the natural prostaglandins. Some of these compounds also inhibit biological responses normally brought about by prostaglandins. Whether a given compound acts as a prostaglandin mimic or inhibitor can depend on the dose levels involved and the biological system involved. As prostaglandin mimics or inhibitors the compounds of this invention are useful for the study, prevention, amelioration, or cure of a variety of conditions or disorders that involve natural prostaglandins in man or in animals.

Stimulation of certain in vitro smooth muscle preparations is commonly taken as a measure of prostaglandin-like activity Rat stomach (fundus) and uterus are two muscles that are convenient indicators of such activity. Table III lists for several of the 3-pyrrolidinones or 2,4-pyrrolidindiones of this invention the concentration in μg/ml required to induce contractions in these two kinds of smooth muscle with an intensity equivalent to that produced by 1 nanogram/ml (stomach) or 25 nanogram/ml (uterus) of the natural prostaglandin $E_1$.

TABLE III

| Compound | Rat Stomach (μg/ml) | Rat Uterus (μg/ml) |
|---|---|---|
| 12a of Ex. 1 | 0.1 | 10 |
| 27a of Ex. 3 | 0.65 | — |
| 12b of Ex. 4 | .05 | 10–20 |

TABLE III-continued

| Compound | Rat Stomach (μg/ml) | Rat Uterus (μg/ml) |
|---|---|---|
| 12c of Ex. 5 | .05 | 10 |
| 12d of Ex. 6 | — | 5* |
| 24a of Ex. 7 | <5 | — |

*Threshold level.

As prostaglandin mimics, these compounds can be expected to inhibit the secretion of gastric acid and thus find use for the study or treatment of gastric ulcers. Also, having a prostaglandin-like effect on uterine tissue, they are expected to cause abortion or induction of labor, e.g., in farm animals. As mimics of prostaglandin $E_1$, these compounds also are expected to cause bronchodilation. For example, compounds 12a and 27a when administered intravenously to guinea pigs effectively reduce bronchoconstriction induced by intravenous administration of histamine.

Under some conditions some of the compounds of this invention also have biological properties opposite to those of the natural prostaglandins. Prostaglandin $E_1$ causes inflammation when applied directly to skin. Non-steroidal antiinflammatory agents are known to inhibit the in vito synthesis of prostaglandins which are known to be among the natural mediators of inflammation, and at least some steroid antiinflammatory agents have been found to inhibit the cellular release of prostaglandins. Compounds such as 12a, 12b, 12c, and 24a at dose levels of about 2 mg/ear afford some protection from the inflammatory effects induced in mouse ears by topically applied croton oil irritant. In this test these compounds are about 1/10–1/100 as potent as hydrocortisone as topical antiinflammatory agents.

1. A compound of the formula

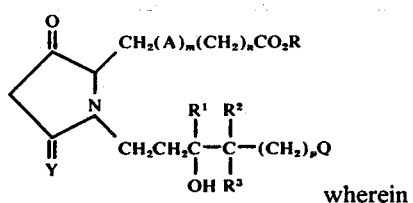

wherein

Y is O or $H_2$;
A is CH=CH, C≡C or phenylene;
m is 0 or 1;
n is 0–6;
R is H, alkali metal, amine salt, alkyl or cycloalkyl of up to 12 carbons;
$R^1$ is H, $CH_3$, $C_2H_5$, $CH=CH_2$ or C≡CH;
$R^2$ and $R^3$ individually are H, F, $CH_3$ or $C_2H_5$;
p is 0–6; and
Q is $CH_3$, $CF_2CH_3$, $CF_3$, phenyl or phenyl substituted with up to two halogens or alkyls of 1–4 carbons;
with the provisos that when $R^1$ is not H then $R^2$ and $R^3$ are each H; and
that when Q is phenyl or substituted phenyl p is 0–3.

2. A compound of claim 1 where Y=$H_2$.

3. A compound of claim 1 where m=0 and n=5.

4. A compound of claim 1 where m=1 and n=2–4.

5. A compound of claim 1 where R is H, alkali metal, amine salt or alkyl or cycloalkyl of 1–4 carbons.

6. A compound of claim 1 where Q is $CH_3$ or $CF_3$ and p=3–5.

7. A compound of claim 1 where Q is $CF_2CH_3$ and p = 2–4.

8. A compound of claim 1 wherein Q is phenyl or substituted phenyl and p = 0–3.

9. The compound of claim 1 which is named 7[N-(3-hydroxy-n-octyl) pyrrolidine-3-one-2-yl]heptanoic acid.

10. The compound of claim 1 which is named 7[N-(3-hydroxy-n-decyl) pyrrolidin-3-one-2-yl]heptanoic acid.

11. The compound of claim 1 which is named 7[N-(3-hydroxy-8,8,8-trifluoro-n-octyl)pyrrolidin-3-one-2-yl]heptanoic acid.

12. The compound of claim 1 which is named 7[N-(3-hydroxy-5-phenyl-n-pentyl)pyrrolidin-3-one-2-yl]heptanoic acid.

13. The compound of claim 1 which is named 7[N-(3-hydroxy-n-octyl)-2,4-dioxopyrrolidin-5-yl]heptanoic acid.

* * * * *